US012414738B2

(12) United States Patent
Lazou et al.

(10) Patent No.: US 12,414,738 B2
(45) Date of Patent: Sep. 16, 2025

(54) INSOLE LAYER FOR MONITORING HUMAN LOWER LIMB AND FOOT PERFORMANCE

(71) Applicant: SportScientia Pte. Ltd., Singapore (SG)

(72) Inventors: Panayiotis Lazou, Limassol (CY); Andrew Gray, Lilli Pilli (AU); Kaspar Lauri, Harjumaa (EE); Erki Koplimets, Harjumaa (EE); Kristjan Tozen, Tallinn (EE); Henri Lumiste, Harjumaa (EE)

(73) Assignee: SPORTSCIENTIA PTE. LTD., Singapore (SG)

( * ) Notice: Subject to any disclaimer, the term of this patent is extended or adjusted under 35 U.S.C. 154(b) by 782 days.

(21) Appl. No.: 17/485,207

(22) Filed: Sep. 24, 2021

(65) Prior Publication Data

US 2022/0087364 A1 Mar. 24, 2022

Related U.S. Application Data

(60) Provisional application No. 63/082,754, filed on Sep. 24, 2020.

(51) Int. Cl.
*A61B 5/00* (2006.01)
*A43B 3/34* (2022.01)
(Continued)

(52) U.S. Cl.
CPC .............. *A61B 5/6807* (2013.01); *A43B 3/34* (2022.01); *A43B 13/22* (2013.01); *A43B 17/14* (2013.01);
(Continued)

(58) Field of Classification Search
None
See application file for complete search history.

(56) References Cited

U.S. PATENT DOCUMENTS 6,498,994 B2 * 12/2002 Vock ..................... G01P 3/42
73/488
8,739,639 B2 6/2014 Owings
(Continued)

FOREIGN PATENT DOCUMENTS

WO 2019175899 A1 9/2019

OTHER PUBLICATIONS

Shokri S et al.: "Recent Advances in Wearable Sensors with Application in Rehabilitation Motion Analysis," arxiv.org, Cornell University Library, 201 Olin Library Cornell University Ithaca, NY 14853, Sep. 13, 2020 (Sep. 13, 2020), XP081762119.
(Continued)

*Primary Examiner* — Aurelie H Tu
(74) *Attorney, Agent, or Firm* — NIXON PEABODY LLP

(57) ABSTRACT

An insole layer includes a top cover layer, a bottom cover layer, and a flexible printed circuit board disposed between the top cover layer and the bottom cover layer. The flexible printed circuit board includes a motion-tracking device, a processor, and a power supply. The motion-tracking device includes a plurality of sensors, wherein each sensor is configured to detect motion of one of a plurality of sensing areas disposed adjacent to a lower surface of the flexible printed circuit board. The processor is configured to receive motion data generated by the motion-tracking device. The power supply device is coupled to the motion-tracking device and the processor.

30 Claims, 25 Drawing Sheets

(51) Int. Cl.

| | | |
|---|---|---|
| *A43B 13/22* | (2006.01) | |
| *A43B 17/14* | (2006.01) | |
| *A61B 5/103* | (2006.01) | |
| *A61B 5/11* | (2006.01) | |
| *G01P 13/00* | (2006.01) | |
| *G06N 20/00* | (2019.01) | |
| *H02J 7/00* | (2006.01) | |
| *H05K 1/03* | (2006.01) | |
| *H05K 1/18* | (2006.01) | |

(52) U.S. Cl.
 CPC ......... *A61B 5/1038* (2013.01); *A61B 5/1107* (2013.01); *A61B 5/112* (2013.01); *A61B 5/486* (2013.01); *A61B 5/7203* (2013.01); *A61B 5/725* (2013.01); *A61B 5/7267* (2013.01); *G01P 13/00* (2013.01); *G06N 20/00* (2019.01); *H02J 7/0042* (2013.01); *H05K 1/0366* (2013.01); *H05K 1/182* (2013.01); *H05K 1/189* (2013.01); *H05K 2201/09036* (2013.01); *H05K 2201/10037* (2013.01); *H05K 2201/10098* (2013.01); *H05K 2201/10151* (2013.01)

(56) References Cited

U.S. PATENT DOCUMENTS

| | | |
|---|---|---|
| 9,763,489 B2 | 9/2017 | Amos |
| 10,182,744 B2 | 1/2019 | Amos |
| 10,357,078 B2 | 7/2019 | Rice |
| 10,398,189 B2 | 9/2019 | Amos |
| 10,674,782 B2 | 6/2020 | Molyneux |
| 11,026,469 B2 | 6/2021 | Molyneux |
| 2003/0097878 A1* | 5/2003 | Farringdon ............... A43B 3/44 73/819 |
| 2009/0137933 A1* | 5/2009 | Lieberman ............ A61B 5/1117 600/595 |
| 2011/0054359 A1* | 3/2011 | Sazonov ................ A61B 5/1118 600/595 |
| 2011/0175744 A1* | 7/2011 | Englert .................. A43B 11/00 702/41 |
| 2012/0079740 A1* | 4/2012 | Zhou .................... A43B 13/141 36/43 |
| 2013/0102937 A1* | 4/2013 | Ehrenreich ........ A61H 23/0236 601/47 |
| 2013/0172722 A1* | 7/2013 | Ninane ................ A61B 5/6803 600/383 |
| 2013/0213145 A1* | 8/2013 | Owings .................. G01L 1/225 73/862.046 |
| 2014/0174205 A1* | 6/2014 | Clarke ................. A61B 5/1038 73/862.626 |
| 2014/0326085 A1* | 11/2014 | Lee ........................ A61B 5/112 73/865.4 |
| 2015/0330855 A1* | 11/2015 | Daniecki ................ G01L 19/147 73/725 |
| 2018/0192514 A1* | 7/2018 | Seo ....................... H05K 1/0281 |
| 2019/0246734 A1 | 8/2019 | Nurse |
| 2021/0219909 A1* | 7/2021 | Ostrow .................. A61B 5/021 |

OTHER PUBLICATIONS

Communication pursuant to Article 94(3) EPC in EP Application No. 21 791 009.0-1113 mailed Nov. 7, 2024 (9 pgs).

\* cited by examiner

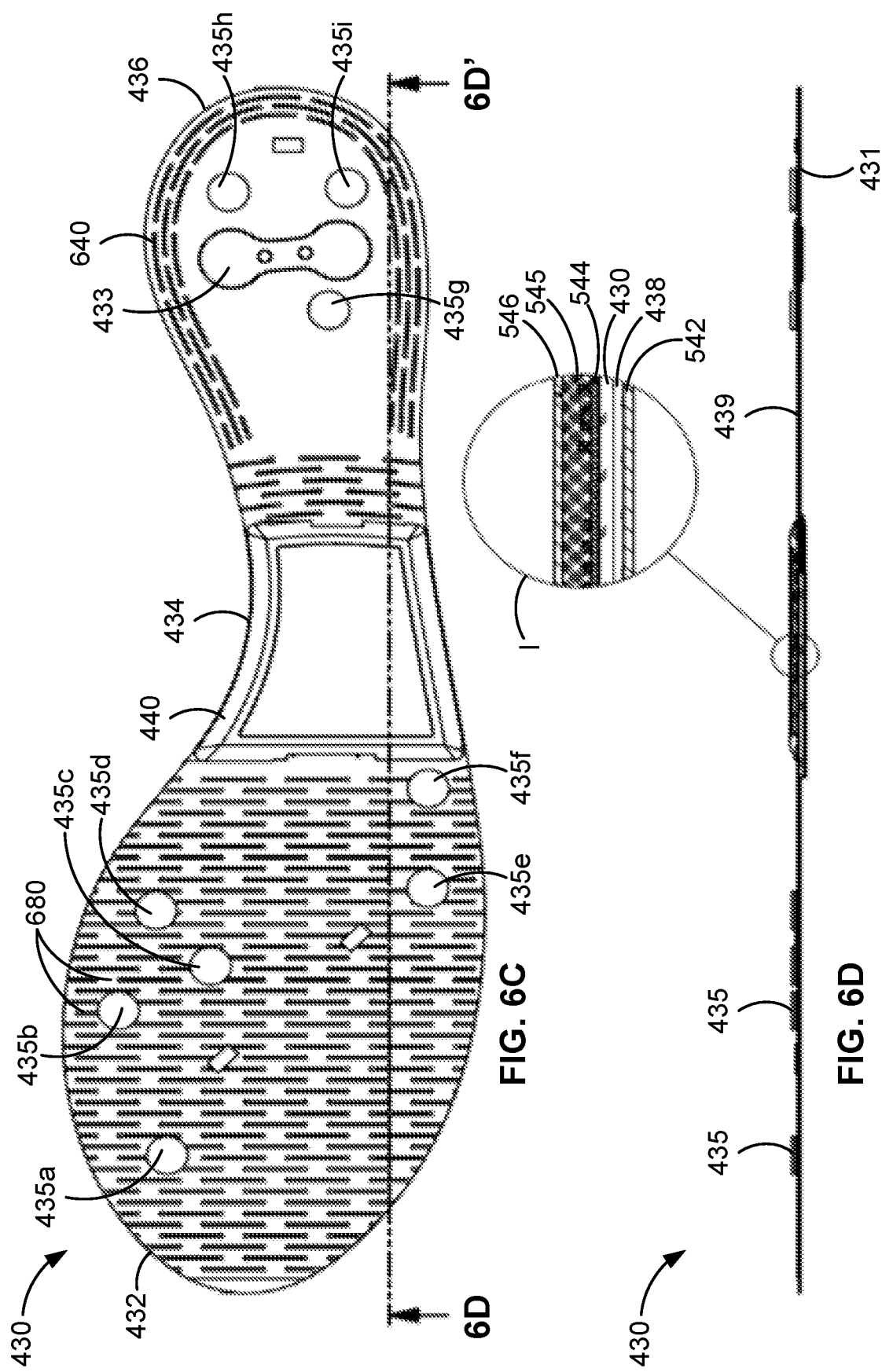

INSOLE LAYER FOR MONITORING HUMAN LOWER LIMB AND FOOT PERFORMANCE

CROSS-REFERENCE TO RELATED APPLICATIONS

This application claims the benefit of, and priority to, U.S. Provisional Patent Application No. 63/082,754 filed on Sep. 24, 2020, which is hereby incorporated by reference herein in its entirety.

FIELD OF THE INVENTION

The present invention relates generally to monitoring human health metrics, and more specifically, to an insole layer for monitoring human lower limb and foot performance using sensors in the insole layer.

BACKGROUND OF THE INVENTION

Sports injuries are commonly caused by poor training methods, structural abnormalities, weakness in muscles, tendons, ligaments, and unsafe training environments. It is imperative to receive continuous assessments of athletes during training and open play during a match such that any assumptions related to performance and injury be validated. As an example, 'athlete load' and other markers related to intensity of movements often rely on acceleration characteristics of the upper portion of the back as measured by a Global Positioning System (GPS) device. This assumes that intensity of movements are solely a function of acceleration characteristics as a substitute for the ground reaction forces, and therefore, provides a wholesome understanding of vulnerability to any specific injury. However, GPS devices have limited ability to reveal how much load is experienced in any specific anatomical structure from foot to neck, and should only be one consideration when assessing 'athlete load', performance, and risk of injury.

While evidence-based research in sports medicine has become an important component of minimizing injury risk and providing rehabilitative care after injury, there remains an ongoing need to develop systems and methods that monitor and record high-quality evidential data in order to make the prevention and treatment of injuries more impactful. In particular, systems and methods that monitor and record data not only in controlled environments of the clinic, but also during training and open play would help provide a continuous stream of real-time and environmental data that can address any gap in understanding the dynamics of performance before, during, after, and even in absence of injury. Such data would help determine external parameters of performance and internal parameters of how the body is responding to the demands of training and open play. While the external parameters are the face-value markers that can be used as performance snapshots relating to overall intensity and tactical play, the internal parameters provide information about risk of injury and thus may provide a basis of specific conditioning and rehabilitation after a training or playing session.

SUMMARY OF THE INVENTION

The term embodiment and like terms, e.g., implementation, configuration, aspect, example, and option, are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter. This summary is also not intended to be used in isolation to determine the scope of the claimed subject matter. The subject matter should be understood by reference to appropriate portions of the entire specification of this disclosure, any or all drawings, and each claim.

According to certain aspects of the present disclosure, an insole layer includes a top cover layer, a bottom cover layer, and a flexible printed circuit board disposed between the top cover layer and the bottom cover layer. The flexible printed circuit board includes a motion-tracking device, a processor, and a power supply. The motion-tracking device includes a plurality of sensors, wherein each sensor is configured to detect motion of one of a plurality of sensing areas disposed adjacent to a lower surface of the flexible printed circuit board. The processor is configured to receive motion data generated by the motion-tracking device. The power supply device is coupled to the motion-tracking device and the processor.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims. Additional aspects of the disclosure will be apparent to those of ordinary skill in the art in view of the detailed description of various embodiments, which is made with reference to the drawings, a brief description of which is provided below.

BRIEF DESCRIPTION OF THE DRAWINGS

The disclosure, and its advantages and drawings, will be better understood from the following description of representative embodiments together with reference to the accompanying drawings. These drawings depict only representative embodiments, and are therefore not to be considered as limitations on the scope of the various embodiments or claims.

FIG. 6C is a bottom view of the flexible printed circuit board of FIG. 6A disposed within the insole layer of FIG. 4A, according to certain aspects of the present disclosure.

FIG. 6D is a side view of the flexible printed circuit board of FIG. 6A disposed within the insole layer of FIG. 4A, according to certain aspects of the present disclosure.

Figure 1:
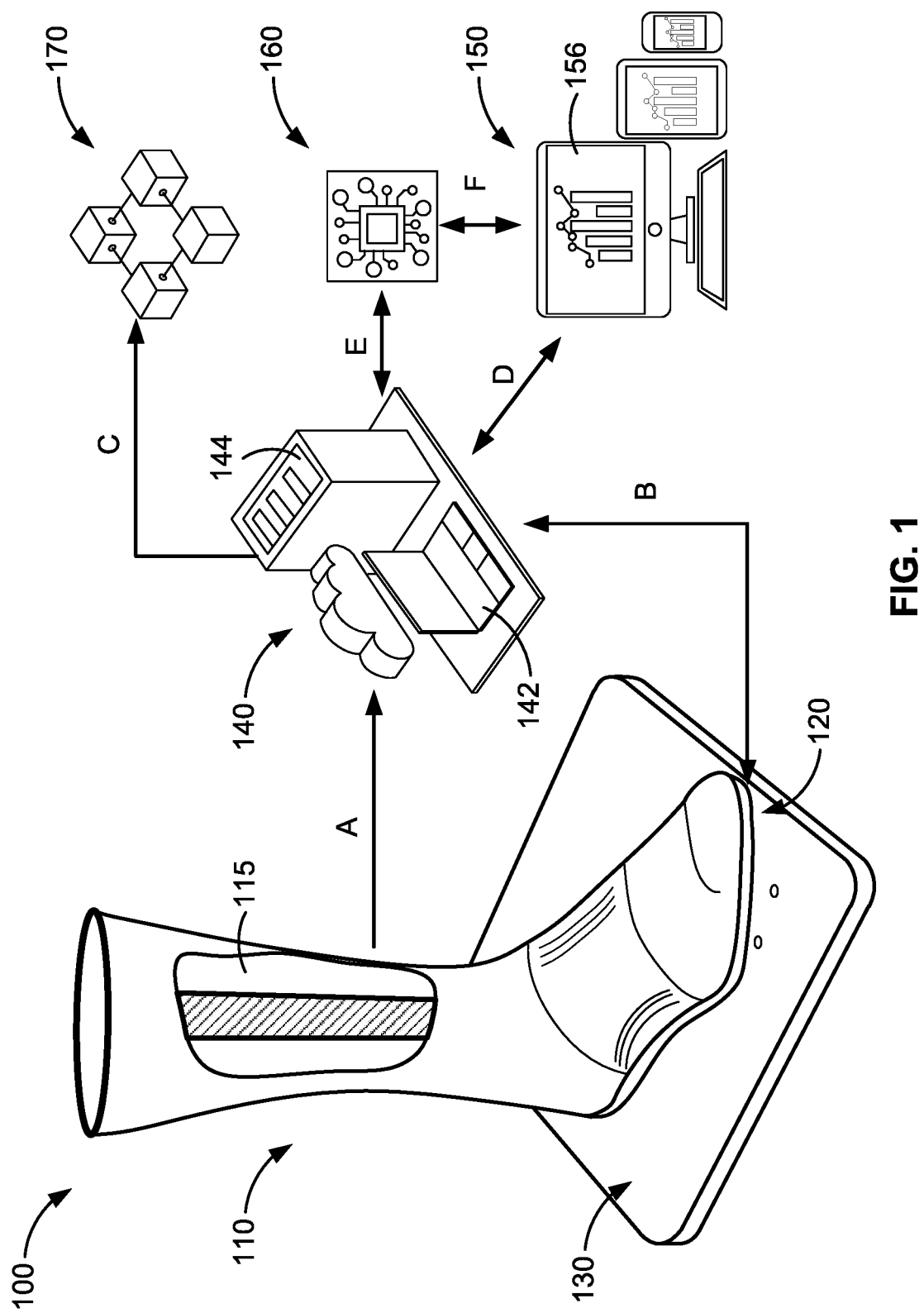
FIG. 1 is a schematic representation of a motion analytics system having a sock with an insole layer for capturing motion data of a user, according to certain aspects of the present disclosure.

The present disclosure is susceptible to various modifications and alternative forms, and some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION

Various embodiments are described with reference to the attached figures, where like reference numerals are used throughout the figures to designate similar or equivalent elements. The figures are not necessarily drawn to scale and are provided merely to illustrate aspects and features of the present disclosure. Numerous specific details, relationships, and methods are set forth to provide a full understanding of certain aspects and features of the present disclosure, although one having ordinary skill in the relevant art will recognize that these aspects and features can be practiced without one or more of the specific details, with other relationships, or with other methods. In some instances, well-known structures or operations are not shown in detail for illustrative purposes. The various embodiments disclosed herein are not necessarily limited by the illustrated ordering of acts or events, as some acts may occur in different orders and/or concurrently with other acts or events. Furthermore, not all illustrated acts or events are necessarily required to implement certain aspects and features of the present disclosure.

For purposes of the present detailed description, unless specifically disclaimed, and where appropriate, the singular includes the plural and vice versa. The word "including" means "including without limitation." Moreover, words of approximation, such as "about," "almost," "substantially," "approximately," and the like, can be used herein to mean "at," "near," "nearly at," "within 3-5% of," "within acceptable manufacturing tolerances of," or any logical combination thereof. Similarly, terms "vertical" or "horizontal" are intended to additionally include "within 3-5% of" a vertical or horizontal orientation, respectively. Additionally, words of direction, such as "top," "bottom," "left," "right," "above," and "below" are intended to relate to the equivalent direction as depicted in a reference illustration; as understood contextually from the object(s) or element(s) being referenced, such as from a commonly used position for the object(s) or element(s); or as otherwise described herein. Further, it is noted that the term "signal" means a waveform (e.g., electrical, optical, magnetic, mechanical or electromagnetic) capable of traveling through a medium such as DC, AC, sinusoidal-wave, triangular-wave, square-wave, vibration, and the like.

Embodiments of the disclosure are directed to an insole layer for monitoring human lower limb and foot performance. The insole layer includes a number of sensors including force-sensitive resistors distributed across a front portion, a middle portion, and a rear portion thereof, as well as three-axis accelerometers, three-axis gyroscopes, magnetometers, electromyopgraphy sensors, and the like. These sensors, as well as the sensors on the sock are configured to generate data associated with the motion of the user. The data may be encrypted and uploaded to a block chain, or an external computing device. The external computing device performs a data analytics routine to provide output data for context and insight on the motion to the user. The output of the data analytics routine may be used to present interactive visualizations on the motion of the user, as well as provide a predictive feedback on the motion of the feet of the user. The predictive feedback may be determined by a machine learning algorithm. Various beneficial features of the sock, the insole layer, and the data analytics method are discussed below, or will become obvious in light thereof.

Referring to the drawings, FIG. 1 is a schematic representation of a motion analytics system 100 having a footwear device with one or more sensors. In the non-limiting embodiment depicted in FIG. 1, the footwear device is a sock 110 with an insole layer 120 having sensors for capturing motion data of a user. The sock 110 includes an electronic pad 115, which is configured to protect a shin bone of the user and may include any number of sensors for capturing motion data of the user. In different embodiments, the footwear device may include only the insole layer 120, or only the sock 110 with a number of sensors but without the insole layer 120. In the embodiment shown in FIG. 1, the sock 110 with the electronic pad 115 and the insole layer 120 is placed over a charging module 130 to charge a power supply device in the insole layer 120 and/or the sock 110. Various embodiments and features of the sock 110 and the insole layer 120 are described in further detail below.

In some embodiments, the motion data may be continuous time series data, while in others, the motion data may be discrete in nature obtained at predetermined time intervals. The sock 110 and/or the insole layer 120 are individually capable of and configured to process and/or upload motion data generated by the sensors therein, to an external computing device 140, a user computing device 150, or a block chain 170. In non-limiting examples, processing of the motion data includes pre-processing, sorting, filtering, compiling, encrypting, decrypting the data as well as computing parameters, statistics, metrics, analytics, etc. using the motion data. Such processing of the motion data may also be performed by the external computing device 140 or the user computing device 150, preferably with the aid of a remote machine learning processor 160.

The sock 110 is connected to the external computing device 140 through a first communication channel A, while the insole layer 120 is connected to the external computing device 140 through a second communication channel B. The external computing device 140 is connected to the block chain 170 by a third communication channel C, and to the user computing device 150 by a fourth communication channel D. The external computing device 140 is connected to the remote machine learning processor 160 by a fifth communication channel E, while the user computing device 150 is connected to the remote machine learning processor 160 by a sixth communication channel F. All communication channels A, B, C, D, E, and F are bidirectional in nature, though in some embodiments, as shown in FIG. 1, the communication channels A and B may be unidirectional. In preferred embodiments, any one or any combination of the communication channels A, B, C, D, E, and F form a network that may include one or more cellular networks, satellite networks and/or computer networks such as, for example, a wide area network, a local area network, personal area network, a global positioning system and combinations thereof. Suitable local area networks may include wired Ethernet and/or wireless technologies such as, for example, wireless fidelity (Wi-Fi). Suitable personal area networks may include wireless technologies such as, for example, IrDA, Bluetooth, Wireless USB, Z-Wave, ZigBee, and/or other near field communication protocols. Suitable cellular networks include, but are not limited to, technologies such as LTE, WiMAX, UMTS, CDMA, and GSM.

The external computing device 140 includes a processor 142 and a memory device 144 coupled to the processor 142. The processor 142 is configured to receive and store the motion data generated by the sock 110 and/or the insole layer 120 through the communication channels A and/or B respectively. The memory device 144 is a non-transitory processor-readable memory and has a machine-readable instruction set for execution by the processor 142 to perform a data analytics method such as, but not limited to, the data analytics method 2000 discussed with respect to FIG. 20 below.

The processor 142 may be any device capable of executing the machine-readable instruction set (e.g., represented by the block diagram of FIG. 20) stored in the non-transitory computer-readable memory device 144. Accordingly, the processor 142 may be an electronic controller, an integrated circuit, a microcontroller, a programmable chip device, a computer, or any other computing device.

The memory device 144 may comprise RAM, ROM, flash memories, hard drives, or any non-transitory memory device capable of storing a machine-readable instruction set which can be accessed and executed by the processor 142. The machine-readable instruction set may comprise logic or algorithm(s) written in any programming language of any generation (e.g., 1GL, 2GL, 3GL, 4GL, or 5GL) such as, for example, machine language that may be directly executed by the processor 142, or assembly language, object-oriented programming (OOP), scripting languages, microcode, etc., that may be compiled or assembled into machine-readable instructions and stored in the non-transitory computer-readable memory device 144. Alternatively, the machine-readable instruction set may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components. While the embodiment depicted in FIG. 1 includes a single memory device 144, other embodiments may include more than one memory device.

The user computing device 150 includes a display 156, as well as a processor and a memory device that are functionally similar to those of the external computing device 140. The display 156 is configured to present interactive visualizations and output data relating to a predictive feedback on the motion of the user. The visualizations and predictive feedback are based on the motion data generated by the sock 110 and/or the insole layer 120. The display 156 may include any medium capable of transmitting a visual output such as, for example, a cathode ray tube, light emitting diodes, liquid crystal displays, plasma displays, or the like. Additionally, the display 156 can be a touch screen that, in addition to providing visual information, detects the presence and location of a tactile input upon a surface of or adjacent to the display and thus provides an input device for a user. Accordingly, the display 156 can receive mechanical input directly upon the optical output provided by the display 156.

The remote machine learning processor 160 is configured to process large amounts of data generated by the sock 110 and/or the insole layer 120 through one or more machine learning algorithms to detect patterns, classify features, and determine one or more predictive feedbacks from user motion. The predictive feedbacks may include information related to any one or any combination of symmetrical distribution of forces on the feet of the user during a motion, likelihood of injury of the user, one or more patterns of injury of the user, a recommended course of action to prevent an injury to the user, among others. The machine learning algorithms may include supervised learning, unsupervised learning, semi-supervised learning, human-in-the-loop learning, reinforcement learning, support vector machine, cluster analysis, hierarchical clustering, anomaly detection, deep learning, convolutional neural networks, and the like. For example, a predictive feedback may be learned from a training data set with motion data and the resulting output. In some embodiments, the motion data generated by the sock 110 and/or the insole layer 120, as well as the processed and analyzed data may be securely stored in the block chain 170. This ensures that the raw motion data and the processed and analyzed motion data are stored as an unfalsifiable, traceable, and time-stamped permanent record of motion of the user. Of course other security measures may be taken such as unique passwords, digital encryption, public/private key signature authentication and the like.

Figure 2A:
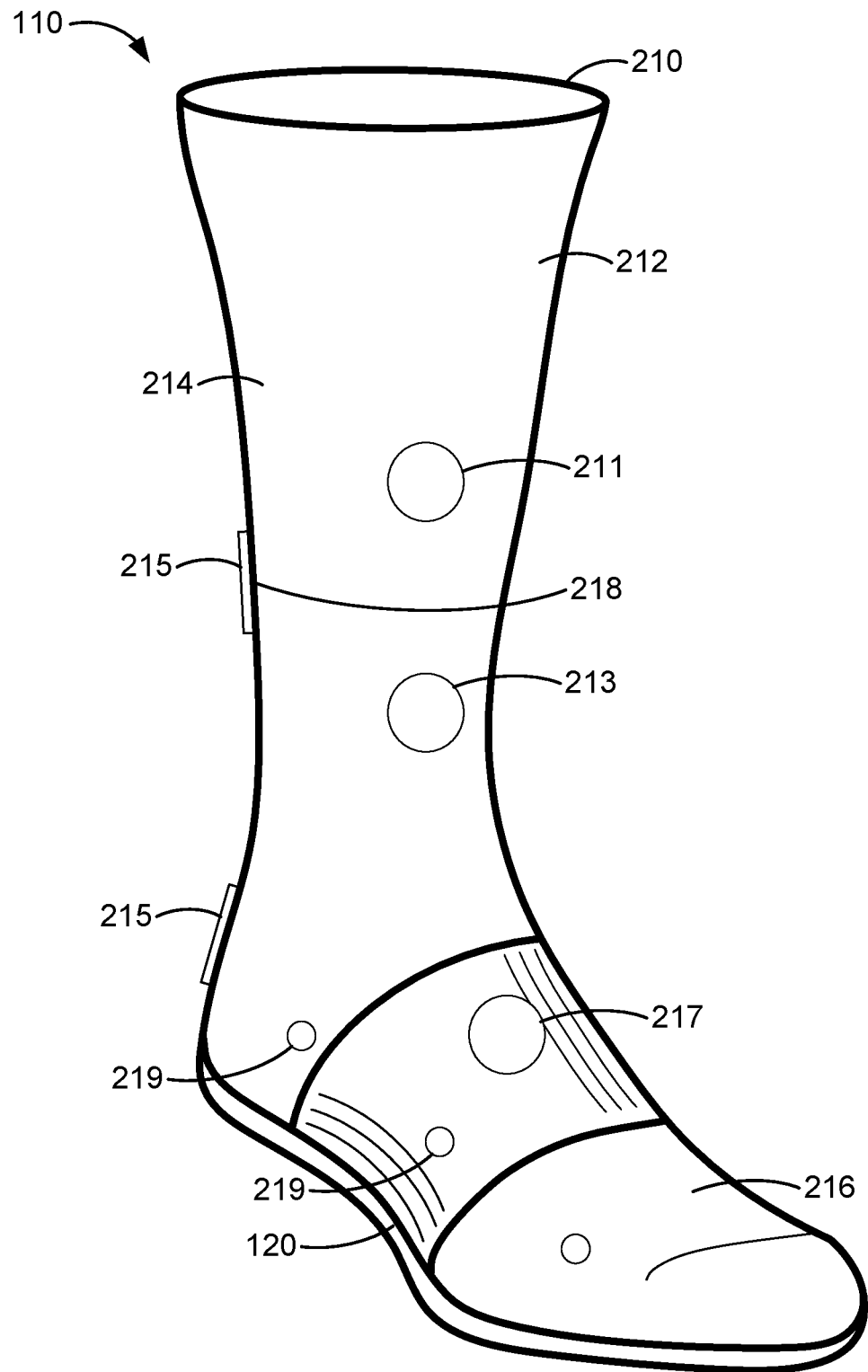
FIG. 2A is a perspective view showing a first embodiment of a sock with an insole layer for capturing motion data of a user, according to certain aspects of the present disclosure.

FIG. 2A is a perspective view showing a first embodiment of the sock 110 for capturing motion data of a user. The sock 110 includes a sock enclosure 210 formed from an elastic composite synthetic fabric. In some embodiments, the elastic composite synthetic fabric is Spandex™, or Revolutional™ by Carvico. Spandex™ is a lightweight polyether-polyurea copolymer and has high elasticity. Revolutional™ is an ultra-thin and breathable synthetic fiber made from micro polyamide and elastane, and is ultraviolet (UV) protective, as well as resistant to chlorine, pilling, sand, and wear and tear. The sock enclosure 210 has a shin portion 212, a calf portion 214, and a foot portion 216.

Figure 2B:
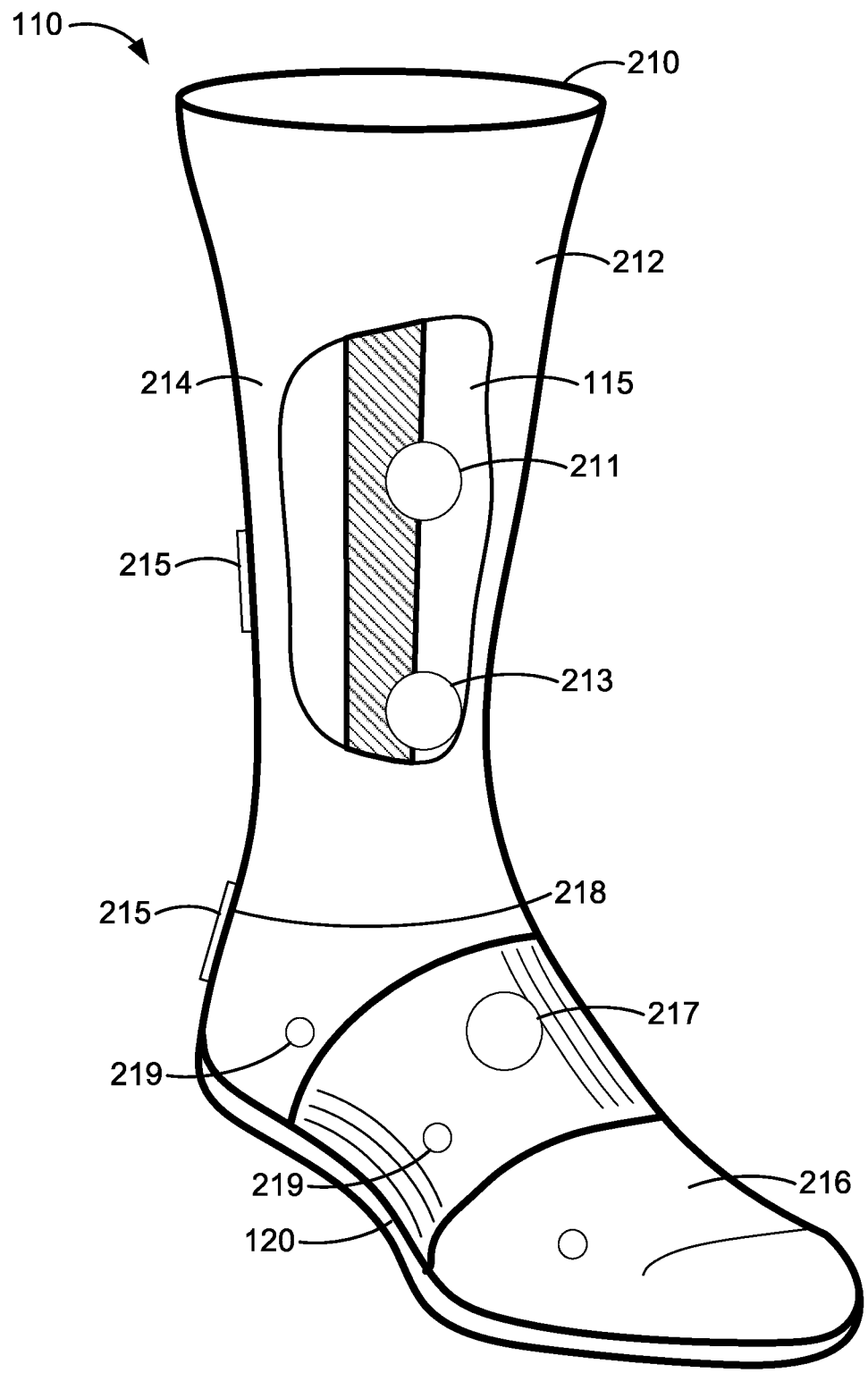
FIG. 2B is a perspective view showing a second embodiment of a sock with an insole layer and an electronic pad for capturing motion data of a user, according to certain aspects of the present disclosure.

The sock 110 includes one or more sensors for capturing the motion data of a user wearing the sock 110. Each of these sensors may be disposed within a biosignal channel 218 of the sock enclosure 210. As a non-limiting example, there may be biosignal channels 218 positioned at a central location and at lower heel-adjacent location along the calf portion 214, as shown in FIGS. 2A-2B. An electromyography (EMG) sensor 215 may be disposed within each of these two biosignal channels 218 along the calf portion 214. The EMG sensors 215 detect physiological data associated with electrical activity produced by one or more leg muscles corresponding to their position along the calf portion 214 and therefore can determine activation of one or more leg muscles, as well as fatigue occurring within such leg muscles.

The sock 110 may include a heart rate sensor 211 and an inertial sensor 213 disposed along the shin portion 212, and a temperature sensor 217 disposed along the foot portion 216. The heart rate sensor 211 is configured to detect a heart rate of the user while wearing the sock 110. The inertial sensor 213 is configured to detect motion data associated with translational and rotational motion of the shin of the user, while using the sock 110. The temperature sensor 217 is configured to detect temperature in the legs of user, while wearing the sock 110. The sock 110 may further include one or more inertial sensors 219 disposed laterally along the foot portion 216. The inertial sensors 213 and 219 detect motion data associated with translational and rotational motion of the legs and feet of the user respectively, and hence relates to forces produced by the one or more leg muscles and feet of the user. In the non-limiting embodiment shown in FIG. 2A, the insole layer 120 is insertable into and disposed along the foot portion 216 of the sock enclosure 210. As described below, the insole layer 120 includes one or more sensors for capturing different aspects of the user's motion.

FIG. 2B is a perspective view showing a second embodiment of the sock 110 for capturing motion data of a user. In addition to the insole layer 120, the sock 110 includes the electronic pad 115 disposed adjacent to the shin portion 212. The electronic pad 115 is communicatively connected to the insole layer 120. The electronic pad 115 includes the heart rate sensor 211 and the inertial sensor 213 embedded therein, in addition to other sensors. The sock 110 has the sock enclosure 210 with a shin portion 212, a calf portion 214, and a foot portion 216. The sock 110 includes one or more sensors that are each disposed within a biosignal channel 218 of the sock enclosure 210. These sensors may include the two or more electromyopgraphy (EMG) sensors 215 disposed along the calf portion 214, as well as the temperature sensor 217 and the inertial sensors 219 disposed laterally along the foot portion 216.

Figure 3:
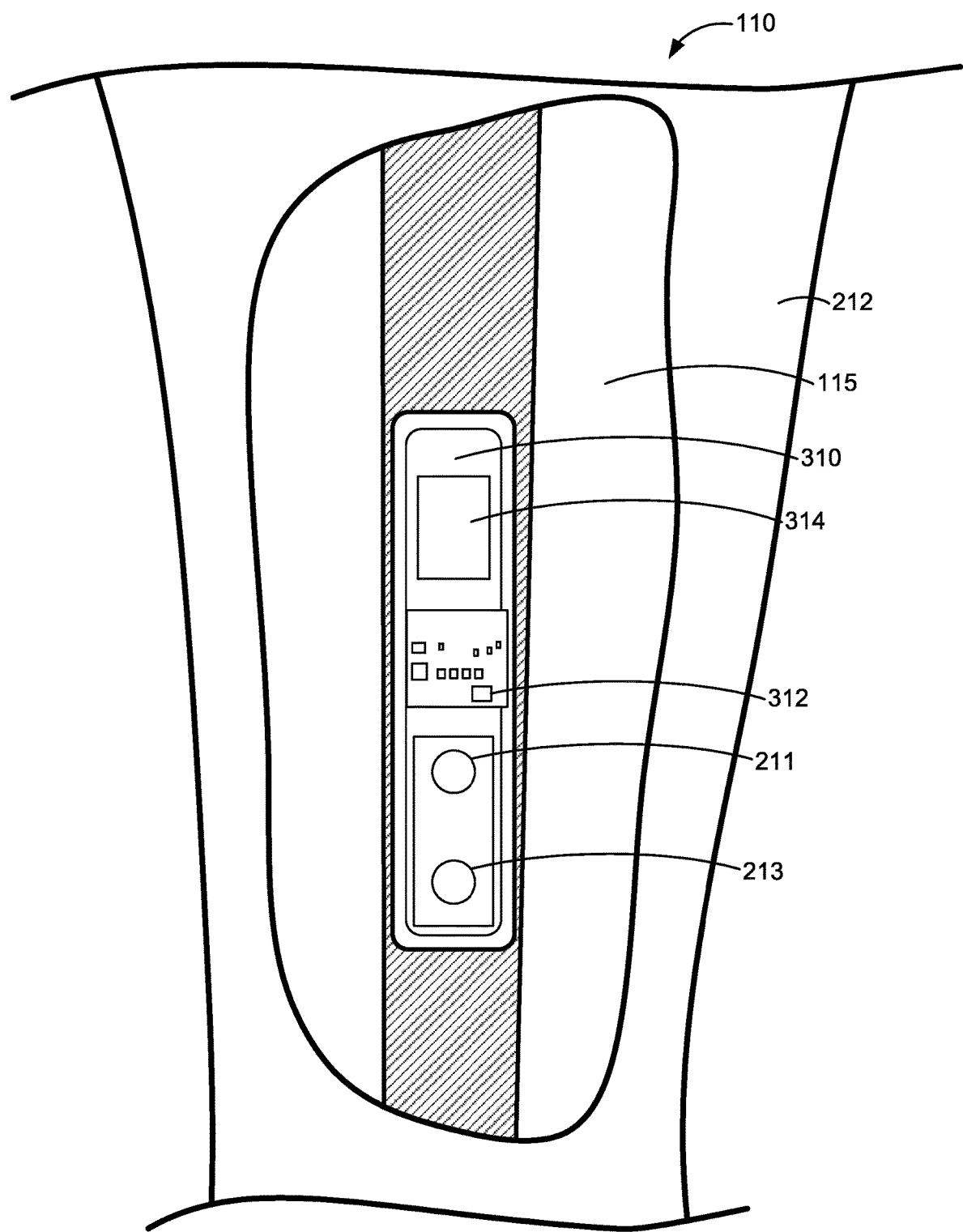
FIG. 3 is a front view showing the electronic pad of FIG. 2B on a sock for capturing motion data of a user, according to certain aspects of the present disclosure.

FIG. 3 is a front view showing the electronic pad 115 in FIG. 2A disposed adjacent to the shin portion 212 on the sock 110. The electronic pad 115 includes a flexible printed circuit board (PCB) 310 on which one or more sensors (e.g., the heart rate sensor 211, the inertial sensor 213) are embedded. Other components such as memory devices, a transceiver, and a network interface may be fabricated on the flexible PCB 310. The flexible PCB 310 may be formed from a glass-reinforced epoxy laminate material such as, but not limited to, FR-4. A processor 312 is disposed on the flexible PCB 310 and configured to receive motion data generated by the sensors and perform pre-processing operations on the raw data. A power supply device 314 such as, but not limited to, an ultra-thin rechargeable lithium polymer battery is also electrically connected therein to provide electrical power to the sensors, the memory devices, the transceiver, and the processor 312. In some embodiments, the flexible PCB 310 may include a charging socket (not shown) for charging the power supply device 314 by direct current (DC) charging, as well as a router device (not shown) for enabling wireless internet communication. Additionally or alternatively, in some embodiments, the flexible PCB 310 may include a radio-frequency (RF) transmitting antenna and a RF receiving antenna (not shown) for bidirectional RF communication from the transceiver that enables both wireless charging of the power supply device 314 and data exchange with the external computing device 140 shown in FIG. 1.

FIGS. 4A-4D represent a perspective view, top view, side view, and bottom view, respectively, of the insole layer 120. In some embodiments, the insole layer 120 has low thickness of between about 0.2 mm and about 0.6 mm, and shaped to be placed inside a shoe (e.g., a military boot, an athletic shoe such as a shoe for soccer, basketball, baseball, running, tennis and the like), a sock (e.g., the sock 110, a regular sock), or under an existing insole of a shoe. In some embodiments, the insole layer 120 has a shape corresponding to a known shoe size (e.g., 9, 9.5, 10, 10.5, 11, 11.5, etc.). In some embodiments, the insole layer 120 has a shape customized to correspond to a user's foot such that any load sensing areas correspond to pressure points on the foot of the user, for maximum comfort.

The insole layer 120 has a top cover layer 410 and a bottom cover layer 420. The top cover layer 410 and the bottom cover layer 420 are water-resistant and designed to protect a flexible PCB 430 disposed between the top cover layer 410 and the bottom cover layer 420. In some embodiments, the top cover layer 410 and the bottom cover layer 420 are formed from a water-resistant polyester material and may include a silicon conformal coating. The top cover layer 410 has a slippery upper surface 411 and a slip-resistant lower surface 419 (shown in FIG. 5). The bottom cover layer 420 has a slippery upper surface 421 (not shown) and a slip-resistant lower surface 429. In some embodiments, the slip-resistant lower surfaces 419 and 429 may be formed by a thin rubber layer disposed under each of the top cover layer 410 and the bottom cover layer 420 respectively.

The flexible PCB 430 is substantially similar to the flexible PCB 310 of the electronic pad 115 and made from a glass-reinforced epoxy laminate material such as, but not limited to, epoxy. The flexible PCB 430 has an upper surface 431, a lower surface 439, a front portion 432, a middle portion 434, and a rear portion 436. A central enclosure 440 for accommodating electronic circuits and devices embedded on the flexible PCB 430 is disposed along the middle portion 434, while a charging socket 433 is disposed along the rear portion 436 of the flexible PCB 430. The flexible PCB 430 further includes a power supply device 438 disposed along the upper surface 431 over the middle portion 434. In non-limiting embodiments, the power supply device 438 may be an ultra-thin rechargeable lithium polymer battery. The lower surface 439 of the flexible PCB 430 may also include a charging socket frame 437 for accommodating a DC charging system (e.g., shown in FIG. 12A) that charges the power supply device 438 through the charging socket 433.

Figure 4A:
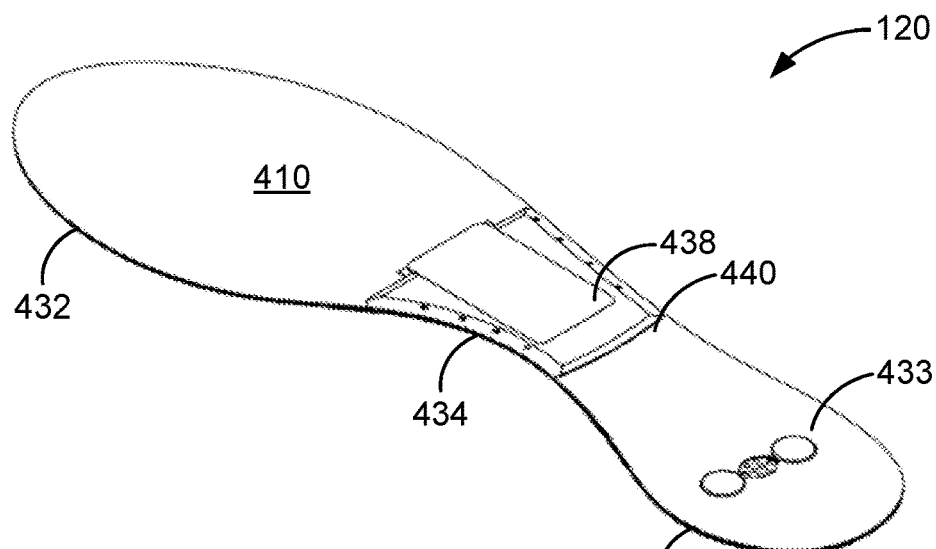
FIG. 4A is a perspective view of an insole layer for capturing motion data of a user, according to certain aspects of the present disclosure.
Figure 4B:
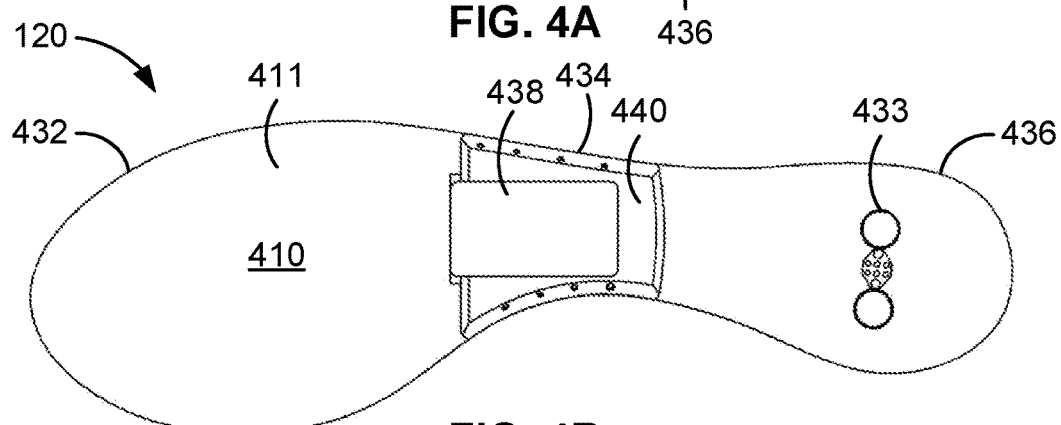
FIG. 4B is a top view of the insole layer of FIG. 4A, according to certain aspects of the present disclosure.
Figure 4C:
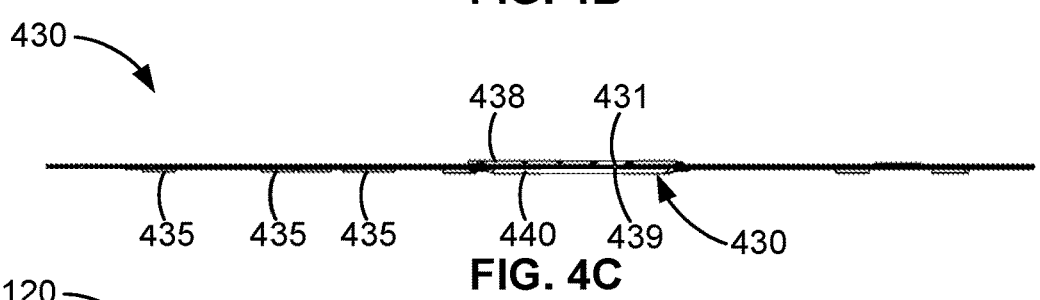
FIG. 4C is a side view of the insole layer of FIG. 4A, according to certain aspects of the present disclosure.
Figure 4D:
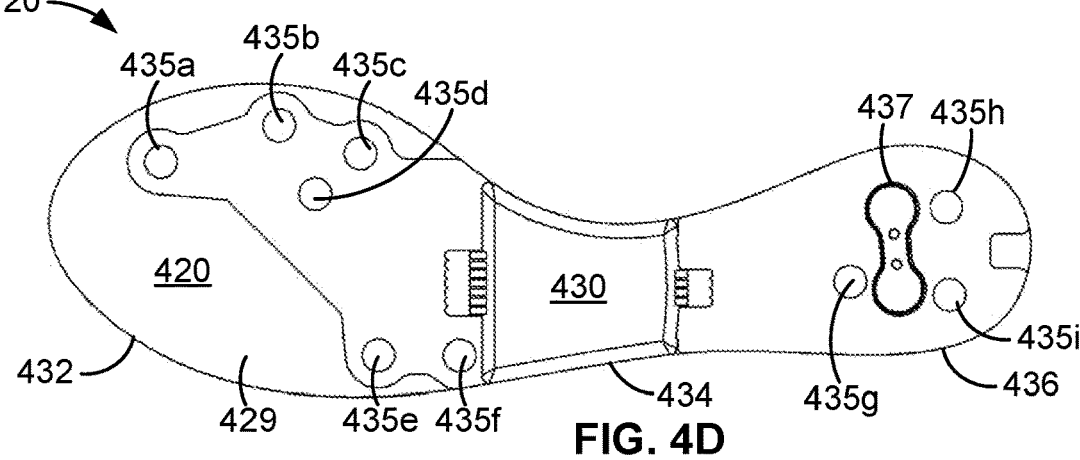
FIG. 4D a bottom view of the insole layer of FIG. 4A, according to certain aspects of the present disclosure.

Multiple sensing areas 435 are distributed adjacent to or along the lower surface 439 of the flexible PCB 430. The sensing areas 435 are each configured to help detect motion and load delivered to and by a user therethrough. The distribution of the sensing areas 435 may be based on commonly known pressure points on a foot or alternatively, customized to correspond with pressure points on the foot of a user based on known physical activity demands of the user. As a non-limiting example, the sensing areas 435 may be grouped in areas that experience the highest load, such as between the first and fifth metatarsal bones and the heel bones. In non-limiting examples, there are nine sensing areas 435a-435i on each insole layer 120 (e.g., as shown in FIG. 4D), but greater or fewer sensing areas may be placed on the insole layer 120. In the non-limiting embodiment of FIG. 4D, the sensing area 435a is positioned adjacent to the big toe of the foot on the front portion 432; the sensing area 435b-435d are positioned on a medial forefoot section of the inner arch of the foot on the front portion 432; the sensing area 435e is positioned on a medial forefoot section of the outer arch of the foot on the front portion 432; the sensing area 435f is positioned on a lateral forefoot section of the outer arch of the foot on the front portion 432; the sensing area 435g is positioned on a mid-heel section of the foot on the rear portion 436; the sensing area 435h is positioned on a lateral heel section of the foot on the rear portion 436; and the sensing area 435i is positioned on a medial-heel section of the foot on the rear portion 436.

Figure 5:
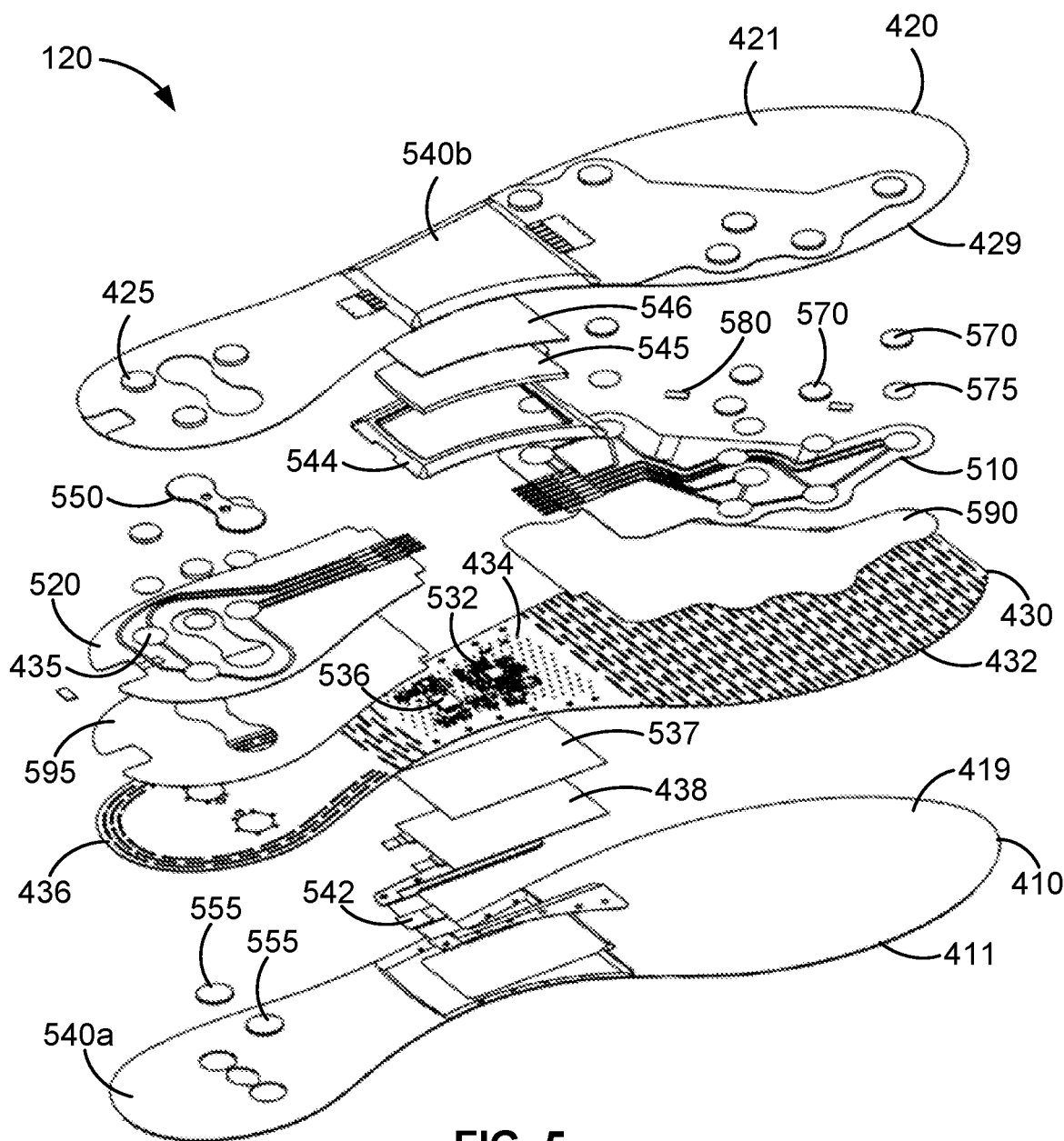
FIG. 5 is an exploded bottom perspective view of the insole layer of FIG. 4A, according to certain aspects of the present disclosure.

FIG. 5 is an exploded bottom perspective view of the insole layer 120. The insole layer 120 has the top cover layer 410 with the upper surface 411 and the lower surface 419. The flexible PCB 430 having the front portion 432, the middle portion 434, and the rear portion 436 is disposed under the top cover layer 410. The flexible PCB 430 also includes a front sensor module 510 and a rear sensor module 520 disposed along the lower surface 439 of the flexible PCB 430 and adjacent to or along the front portion 432 and the rear portion 436 respectively. In this example, the front sensor module 510 includes the sensing areas 435a-435f described above, while the rear sensor module 520 includes the sensing areas 435g-435i described above. The bottom cover layer 420 with the upper surface 421 and the lower surface 429 is disposed under the front sensor module 510 and the rear sensor module 520.

The charging socket frame 437, and an attachment bracket 550 disposed through the charging socket frame 437 are disposed adjacent to the bottom cover layer 420. The attachment bracket 550 is configured to accommodate magnetic attachments 555 of a DC charging station 1220 (shown in FIG. 12B), and is described in further detail below with respect to FIGS. 9A-9B. The bottom cover layer 420 also includes holes 425 for accommodating each of the plurality of sensing areas 435.

The front sensor module 510 and the rear sensor module 520 are covered by a front adhesive film 590 and a rear adhesive film 595 respectively. The front adhesive film 590 and the rear adhesive film 595 are disposed between the flexible PCB 430 and the bottom cover layer 420. In some embodiments, the front adhesive film 590 and the rear adhesive film 595 may be a slip-resistant layer of ethylene propylene diene monomer (EPDM) foam having thickness between about 0.2 mm and about 1.2 mm. The front sensor module 510 and the rear sensor module 520 are described in further detail with respect to FIGS. 7A-7B.

The front sensor module 510 and the rear sensor module 520 include one or more ventilation openings 710 (FIGS. 7A-7B) for ventilating the sensors therein. Each ventilation opening 710 is covered by a waterproof membrane 580, as further discussed and shown with respect to FIG. 8.

Both the front sensor module 510 and the rear sensor module 520 include multiple sensing areas 435. Each sensing area 435 includes a puck-shaped load concentrator 570 encapsulated within a protective adhesive film 575. The load concentrators 570 have force-sensitive resistors therein that can measure load applied to the location on the foot where the sensing area is located. The load concentrators 570 can have different thicknesses for different areas of the foot. For example, the load concentrators adjacent to the rear portion 436 may have a greater thickness than the load concentrators 570 in the metatarsal area adjacent to the middle portion 434.

The flexible PCB 430 includes a motion-tracking device 532, a processor 536, and the power supply device 438 and other electrical components. The motion-tracking device 532 is electronically connected to or includes sensors that detect motion of a user. These sensors include the force-sensitive resistors described above that change resistance upon application of a force, as well as three-axis accelerometers for measuring acceleration and g-forces, three-axis gyroscopes for measuring rotation and angular velocity, magnetometers for measuring trajectory and direction of heading, temperature sensors for measuring temperature of the foot, electromyography sensors for measuring muscle activation and fatigue, and heart sensors for measuring heart rate, all of which measure various physical and physiological parameters of the user. In some embodiments, the three-axis accelerometers include at least one high-G accelerometer. The distribution of sensing points for the force-sensitive resistors may be based on commonly known pressure points on feet or alternatively, customized to correspond with pressure points on the foot of a user based on known physical activity demands of the user. For example, the force-sensitive resistors may have sensing points directly under the heel of the user in the rear portion 436 in order to capture data on translational and rotational motion from an area which experiences a high range of motion. In some embodiments, the force-sensitive resistors are replaceable devices that can be installed after peeling off a sensor cover.

In some embodiments, the force-sensitive resistors have a measuring frequency of about 300 Hz, sensitivity of about 1 Newton, and accuracy of about ±3 Newtons. In some embodiments, the three-axis accelerometers have a measuring frequency of about 300 Hz, a range between about ±2-16 G, and a sensitivity of about 0.06-0.48 mG. In some embodiments, the high-G accelerometers have a measuring frequency of about 300 Hz, a range between about ±100-400 G, and a sensitivity of about 49-195 mG. In some embodiments, the three-axis gyroscopes have a measuring frequency of about 300 Hz, a range between about ±250-2000 dps, and a sensitivity of about 7.6-61 mdps. In some embodiments, the magnetometers have a measuring frequency of about 300 Hz, a range between about ±4900 uT, and a sensitivity of about 0.15 uT. In some embodiments, the temperature sensor in the motion-tracking device 532 is substantially similar to the temperature sensor 217, and measures temperature at frequency of 1 Hz with a sensitivity of about 1 Celsius.

The processor 536 is substantially similar to the processor 142 discussed above. The processor 536 is configured to receive motion data generated by the sensors in the motion-tracking device 532. In a non-limiting example, the processor 536 is a microcontroller having built-in wireless capabilities.

The power supply device 438 is electrically coupled to the motion-tracking device 532 and the processor 536. The power supply device 438 is encapsulated within an adhesive film 537 for protection. The power supply device 438 is configured to power the motion-tracking device 532, the processor 536, and any electrical and electronic devices embedded in the flexible PCB 430.

The central enclosure 440 is disposed along the middle portion 434 of the flexible PCB 430 for housing the motion-tracking device 532, the power supply device 438, the processor 536, and other electronic circuits and devices. The central enclosure 440 has an upper frame 542, a lower frame 544, and a covering plate 546 coupled to the lower frame 544. The upper frame 542 and the lower frame 544 are covered with a protective fabric 540a and a protective fabric 540b respectively. A layer of potting material 545 such as, but not limited to, epoxy resin is disposed within the lower frame 544 and between the covering plate 546 and the flexible PCB 430.

Figure 6A:
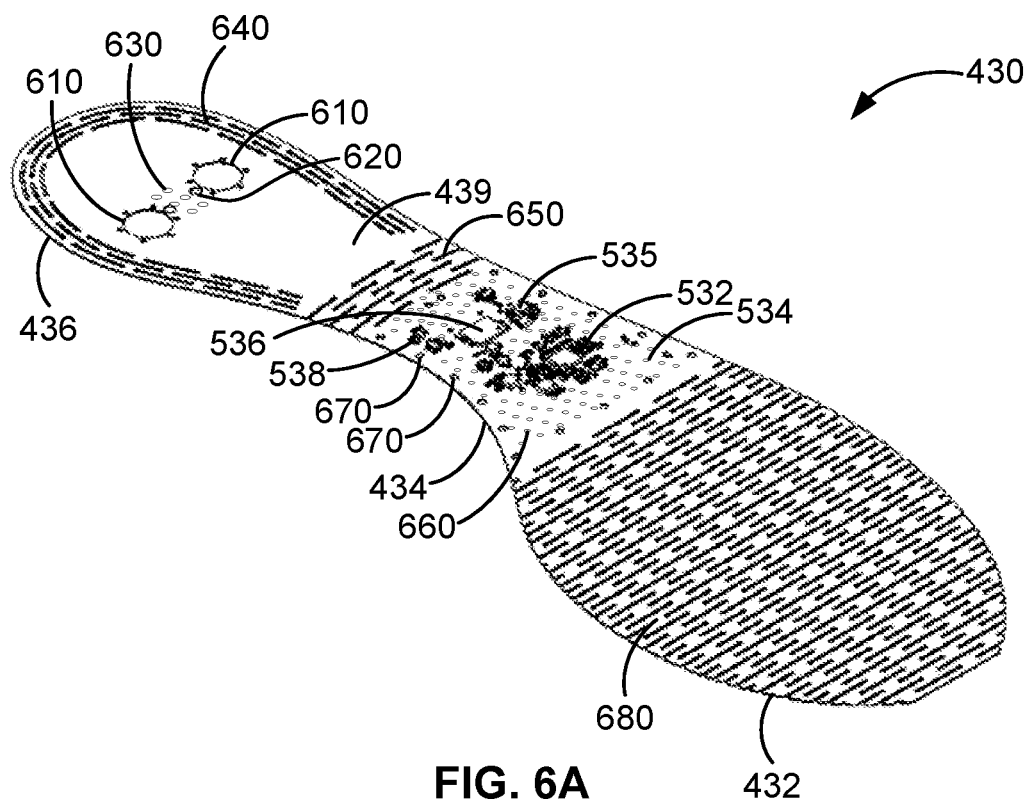
FIG. 6A is a bottom perspective view of a flexible printed circuit board disposed within the insole layer of FIG. 4A, according to certain aspects of the present disclosure.
Figure 6B:
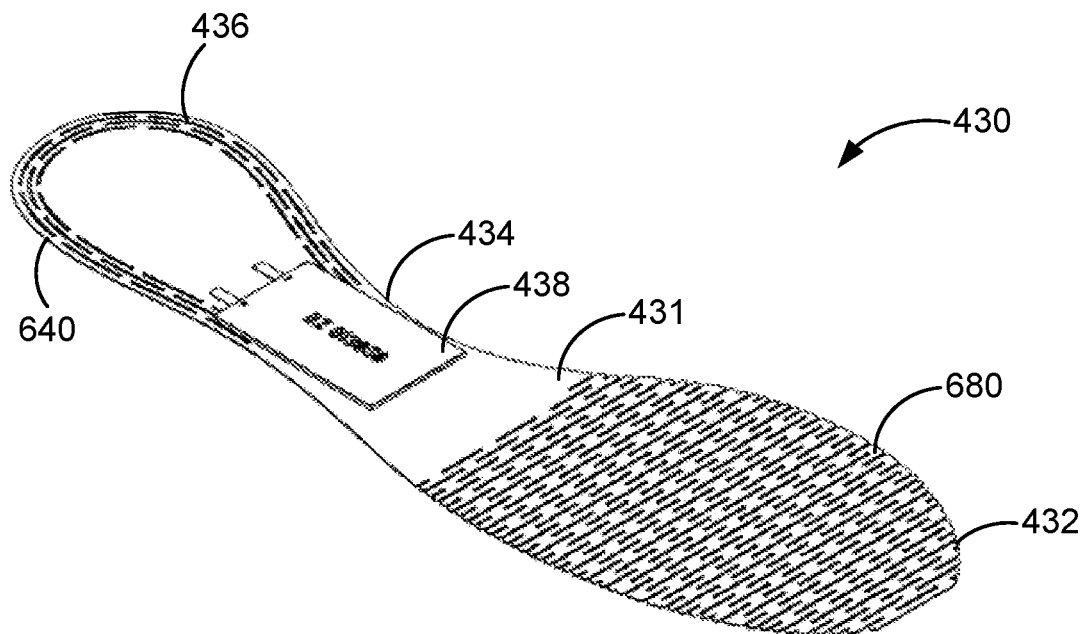
FIG. 6B is a top perspective view of the flexible printed circuit board of FIG. 6A disposed within the insole layer of FIG. 4A, according to certain aspects of the present disclosure.

FIGS. 6A-6D represent a bottom perspective view, a top perspective view, a bottom view, and a side view, respectively, of the flexible PCB 430 disposed within the insole layer 120. While various features and embodiments of the flexible PCB 430 are already discussed above, FIGS. 6A-6D provide additional features and perspectives of the flexible PCB 430. The power supply device 438 is disposed adjacent to or along the upper surface 431 in the middle portion 434 of the flexible PCB 430, while the charging socket 433 is disposed on the upper surface 431 in the rear portion 436 of the flexible PCB 430. The charging socket 433 is configured to charge the power supply device 438 by DC charging. The sensing areas 435 are distributed on the lower surface 439 of the flexible PCB 430 based on pressure points on the foot of a user, as shown in FIGS. 6C-6D.

The central enclosure 440 (shown in FIGS. 4A-4D, and FIG. 6D) is disposed adjacent to or along the lower surface 439 in the middle portion 434 of the flexible PCB 430. The central enclosure 440 houses the motion-tracking device 532 having the plurality of sensors described above, as well as the processor 536 discussed above, a memory device 535, a router device 534, and an energy-harvesting device 538. The energy-harvesting device 538 is configured to convert the kinetic energy generated through movement of the insole layer 120 into electrical energy for charging the power supply device 438.

The memory device 535 is a non-transitory processor-readable memory device that is substantially similar to the memory device 144. In the non-limiting example of FIGS. 4A-6D, the memory device 535 is a flash NAND memory device having at least 128 MB of storage. The memory device 535 stores machine-readable instructions that when executed by the processor 536 causes the processor 536 to encrypt the motion data generated from the motion-tracking device 532 using an Advanced Encryption Standard (AES), and then upload the encrypted data to the block chain 170, or the external computing device 140 and/or the user computing device 150. Additionally, the machine-readable instructions may cause the processor 536 to download data from the external computing device 140 and/or the user computing device 150 and decrypt the downloaded data.

The motion data generated by the motion-tracking device 532 may be used by the processor 536, the external computing device 140, and/or the user computing device 150 to present interactive visualizations on the motion of the user and/or provide predictive feedback on the motion of the feet of the user, determined by a supervised or an unsupervised algorithm based on the motion data. Further, the insole layer 120 can be diagnosed remotely from the external computing device 140 and/or the user computing device 150 using diagnostic data uploaded and downloaded over the wireless communication channels described above.

The router device 534 may include an antenna, a modem, a LAN port, wireless fidelity (Wi-Fi) card, WiMax card, ZigBee card, Bluetooth chip, USB card, mobile communications hardware, and/or other hardware for communicating with other networks and/or devices. The router device 534 enables wireless internet communication between the insole layer 120 and an external device such as the external computing device 140, the user computing device 150, the electronic pad 115 on the sock 110, a compression vest, a wearable device worn by the user such as those made by Apple, Garmin, FitBit, etc. In the non-limiting example of FIGS. 4A-6D, the router device 534 is a 4G/5G IoT (Internet-of-things) modem, which provides low-power operation in an always-connected state (at less than 2 milli amperes of current) and can provide encrypted data uploads many times per day. When the insole layer 120 is operational in remote locations where there is no cellular signal, the motion data can be uploaded using a local Bluetooth network, or may be stored in the memory device 535 until better wireless connection is available.

Additionally, the central enclosure 440 of the flexible PCB 430 may include supporting electronic devices and circuits such as, but not limited to, a charger for recharging the power supply device 438, a DC/DC switching regulator for converting DC power of the power supply device 438 to system power, one or more voltage regulators, a radio-frequency (RF) antenna, a battery protector, a supervisor for the processor 536, and the like.

The flexible PCB 430 further includes a number of physical features. These include one or more cutout portions 610 to accommodate the one or more magnetic attachments 555 of a DC charging station 1220 (shown in FIG. 12B), one or more conductive surfaces/traces 630 for spring-loaded connection pins of the DC charging station 1220, one or more holes 620 to accommodate guide pins of the DC charging station 1220, a cluster of perforations 660 in the middle portion 434 for incorporating the layer of potting material 545, and a series of apertures 670 around a perimeter of the middle portion 434 for positioning the central enclosure 440. Further, the flexible PCB 430 includes kerf bend cuts 640 forming a concave shape around the rear portion 436 of the flexible PCB 430, which results in high transverse flexibility perpendicular to the concave contour; kerf bend cuts 650 for separating the central enclosure 440 from the rear portion 436, which results in high longitudinal flexibility; and kerf bend cuts 680 for enabling longitudinal bending of the front portion 432 of the flexible PCB 430, which results in very high longitudinal and medium transverse flexibility. The kerf bend cuts 640, 650, and 680 allow the FR-4 material of the flexible PCB 430 to be used as a current carrier through the incessant translational, rotational, and shearing movement of the insole layer 120. Additionally, the kerf bend cuts 640, 650, and 680 allow the insole layer 120 to take the shape of the footwear it is placed in, which creates tighter fitting and more precise measurement of motion by the sensors.

FIG. 6D shows a cross-sectional view of the insole layer 120 along the line 6D-6D' in FIG. 6C, showing the various layers of the middle portion 434 stacked over one another from the bottom to the top. FIG. 6D shows an inset I showing the specific layers of the middle portion 434. The covering plate 546 is stacked under the layer of potting material 545, which is stacked under the lower frame 544. The lower frame 544 is stacked under the flexible PCB 430, which is stacked under the power supply device 438, which is stacked under the upper frame 542.

Figure 7A:
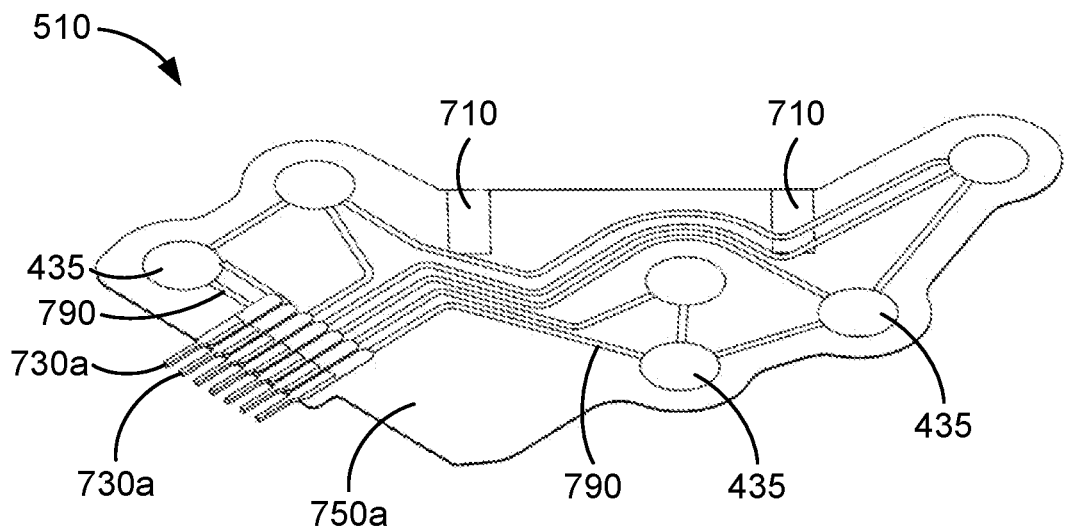
FIG. 7A is a bottom perspective view showing a front sensor module of the flexible printed circuit board of FIG. 6A, according to certain aspects of the present disclosure.

FIG. 7A is a bottom perspective view showing the front sensor module 510 of the flexible PCB 430. The front sensor module 510 includes one or more sensing areas 435, connection pins 730*a*, traces 790 connecting the sensing areas 435 with the connection pins 730*a*, and one or more ventilation openings 710 that provide ventilation to the sensors of the flexible PCB 430. The connection pins 730*a* are configure to connect with the central enclosure 440 (FIGS. 4A-4D and FIG. 5). The sensing areas 435 and the ventilation openings 710 are dispersed on a film laminate 750*a* that protects the flexible PCB 430 against tearing.

Figure 7B:
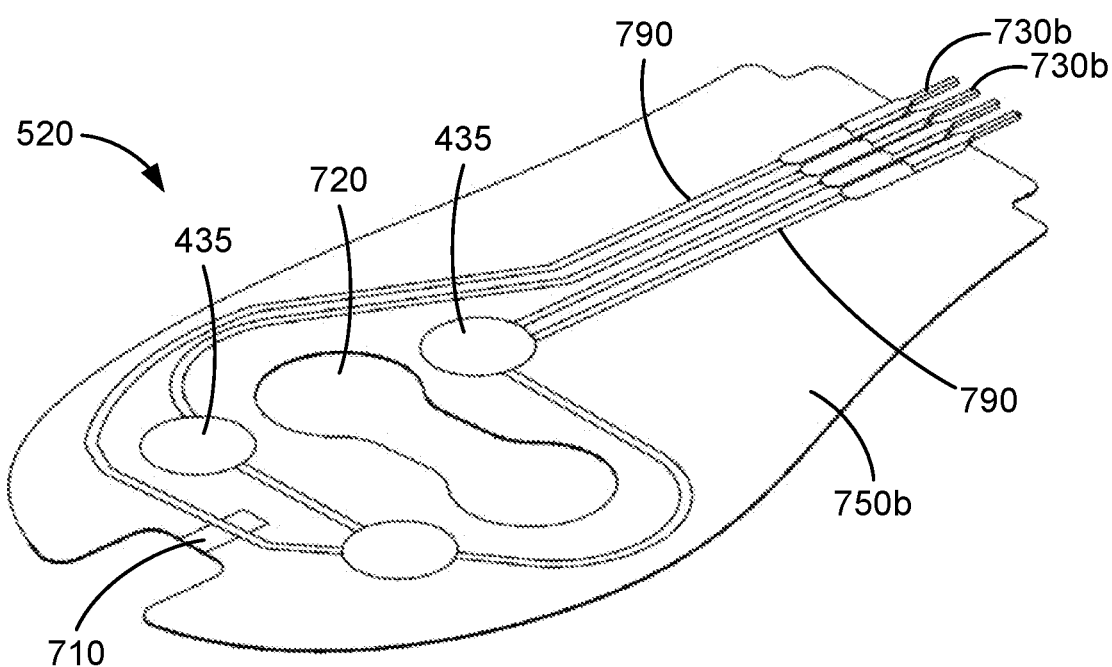
FIG. 7B is a bottom perspective view showing a rear sensor module of the flexible printed circuit board of FIG. 6A, according to certain aspects of the present disclosure.

FIG. 7B is a bottom perspective view showing the rear sensor module 520 of the flexible PCB 430. The rear sensor module 520 includes one or more sensing areas 435, connection pins 730*b*, traces 790 connecting the sensing areas 43 with the connection pins 730*b*, one or more ventilation openings 710 and a cutout 720 for the attachment bracket 550 of the bottom cover layer 420. The connection pins 730*b* are configured to connect with the central enclosure 440. The sensing areas 435 and the ventilation openings 710 are dispersed on a film laminate 750*b* that protects the flexible PCB 430 against tearing.

Figure 8:
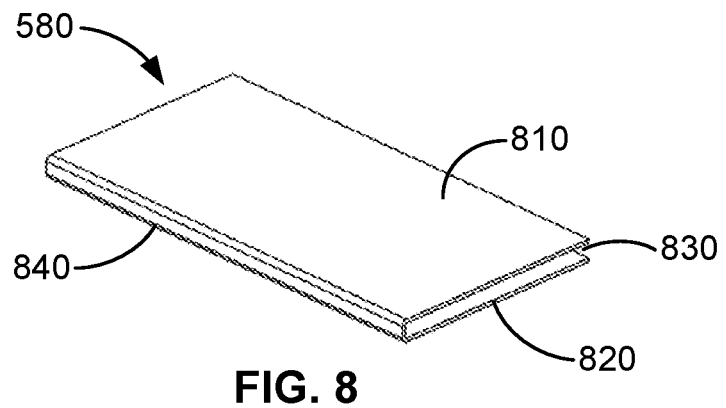
FIG. 8 is perspective view of a waterproof membrane for covering ventilation openings in the front sensor module of FIG. 7A and the rear sensor module of FIG. 7B, according to certain aspects of the present disclosure.

FIG. 8 is perspective view of one of the waterproof membranes 580 in FIG. 5. The waterproof membrane 580 covers one of the ventilation openings 710 in the front sensor module 510 and the rear sensor module 520. Each waterproof membrane 580 includes an open area 830 surrounded by an upper wall 810, a lower wall 820, and a sidewall 840. The open area 830 is placed over one of the ventilation openings 710 in the front sensor module 510 and the rear sensor module 520.

Figures 9A, 9B:
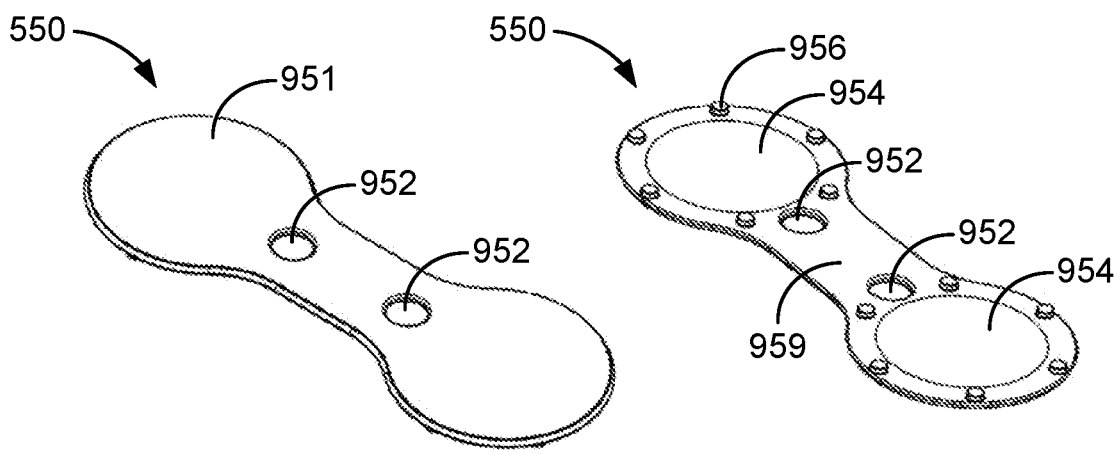
FIG. 9A is a top perspective view showing an attachment bracket of a charging socket of the insole layer of FIG. 4A, according to certain aspects of the present disclosure.
FIG. 9B is a bottom perspective view showing the attachment bracket of FIG. 9A, according to certain aspects of the present disclosure.

FIGS. 9A-9B represent a top perspective view and a bottom perspective view, respectively, showing the attachment bracket 550 on the bottom cover layer 420. The attachment bracket 550 has a top surface 951 and a bottom surface 959. A number of pins 956 are dispersed around a perimeter of the bottom surface 959. The pins 956 aid in positioning and locking the attachment bracket 550 to the bottom cover layer 420. The attachment bracket 550 further includes one or more cutouts 954 for placing the magnetic attachments 555 of the DC charging station 1220 (shown in FIG. 12B) and one or more through-holes 952 to accommodate guide pins of the DC charging station 1220.

Figures 10A, 10B:
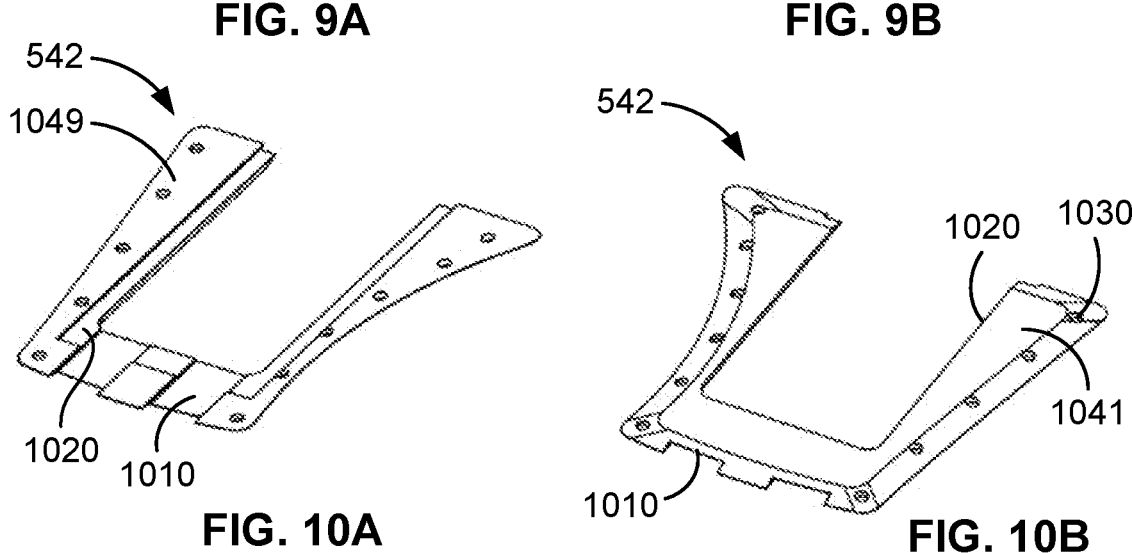
FIG. 10A is a bottom perspective view showing an upper frame of a central enclosure for housing electronics embedded in the flexible printed circuit board, according to certain aspects of the present disclosure.
FIG. 10B is a top perspective view showing the upper frame of FIG. 10A, according to certain aspects of the present disclosure.

FIGS. 10A-10B represent a bottom perspective view and a top perspective view, respectively, showing the upper frame 542 of the central enclosure 440 that covers the power supply device 438. The upper frame 542 has a top surface 1041 and a bottom surface 1049. The upper frame 542 includes one or more cut-outs 1010 for terminals of the power supply device 438, as well as a support edge 1020 to accommodate a thinner section of the power supply device 438. The upper frame 542 further includes a number of pins 1030 dispersed around a perimeter of the bottom surface 1049, which aid in positioning the upper frame 542 with the lower frame 544 and connecting with the flexible PCB 430.

Figures 10C, 10D:
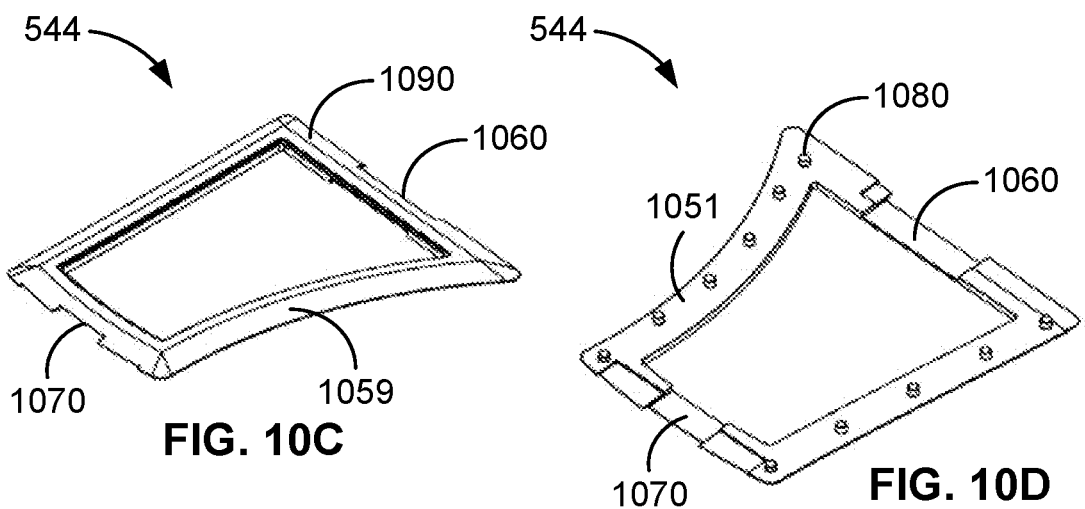
FIG. 10C is a bottom perspective view showing a lower frame of a central enclosure for housing electronics embedded in the flexible printed circuit board, according to certain aspects of the present disclosure.
FIG. 10D is a top perspective view showing the lower frame of FIG. 10C, according to certain aspects of the present disclosure.

FIGS. 10C-10D represent a bottom perspective view and a top perspective view, respectively, showing the lower frame 544 of the central enclosure 440 that covers the electronic circuits and devices therein. The lower frame 544 has a top surface 1051 and a bottom surface 1059. The lower frame 544 includes one or more cut-outs 1060 for connection pins 730a of the front sensor module 510, one or more cut-outs 1070 for connection pins 730b of the rear sensor module 520, and a cut-out 1090 for pouring in potting material to form the layer of potting material 545. The lower frame 544 further includes a number of pins 1080 dispersed around a perimeter of the top surface 1051, which aid in positioning the lower frame 544 with the upper frame 542 and connecting with the flexible PCB 430.

Figure 11A:
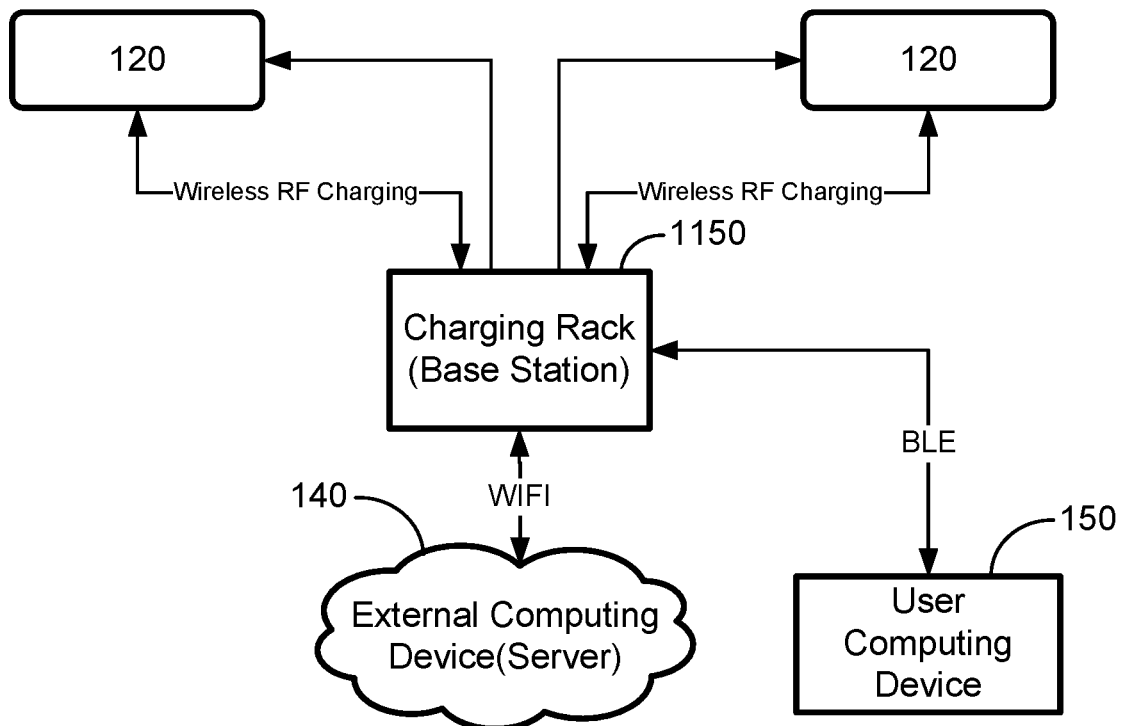
FIG. 11A is a block diagram showing a wireless radio frequency (RF) charging system of the insole layer of FIG. 4A, according to certain aspects of the present disclosure.

As described above, the insole layer 120 has a rechargeable power supply device 438. system, or a direct current (DC) charging system. FIG. 11A is a block diagram of the wireless RF charging system for the insole layer 120. One or more insole layers 120 can be positioned on or adjacent to a charging rack 1150 such that an RF antenna in the insole layer 120 can receive RF transmission for wireless charging. The charging rack serves as a base station that is also wirelessly connected to the external computing device 140 (e.g., by a wireless internet connection) 140 and to the user computing device 150 (e.g., by a Bluetooth Low Energy (BLE) connection, wireless internet connection, etc.). This enables the insole layer 120 to upload motion data generated by the sensors, while the power supply device 438 is recharging.

Figure 11B:
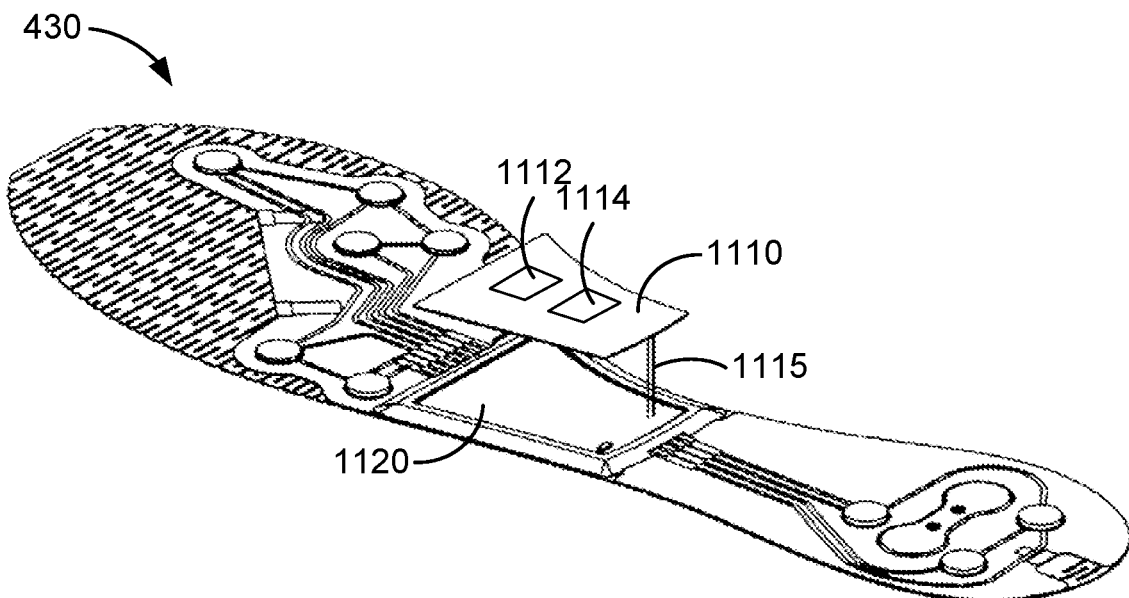
FIG. 11B is a bottom perspective view showing the flexible printed circuit board of FIG. 6A having electronics associated with the wireless RF charging system of FIG. 11A, according to certain aspects of the present disclosure.

FIG. 11B is a bottom perspective view showing the flexible PCB 430 having electronics associated with the wireless RF charging system of FIG. 11A. The flexible PCB 430 has an RF plate 1110 with an embedded RF transmitting antenna 1112 and an embedded RF receiving antenna 1114. The RF plate 1110 is electrically connected to an RF chip 1120 embedded in the layer of potting material 545 through connection lines 1115. The RF transmitting antenna 1112 and the RF receiving antenna 1114 are configured for bidirectional communication that enables both data exchange with the external computing device 140 and/or the user computing device 150, as well as wireless charging of the power supply device 438.

Figure 12A:
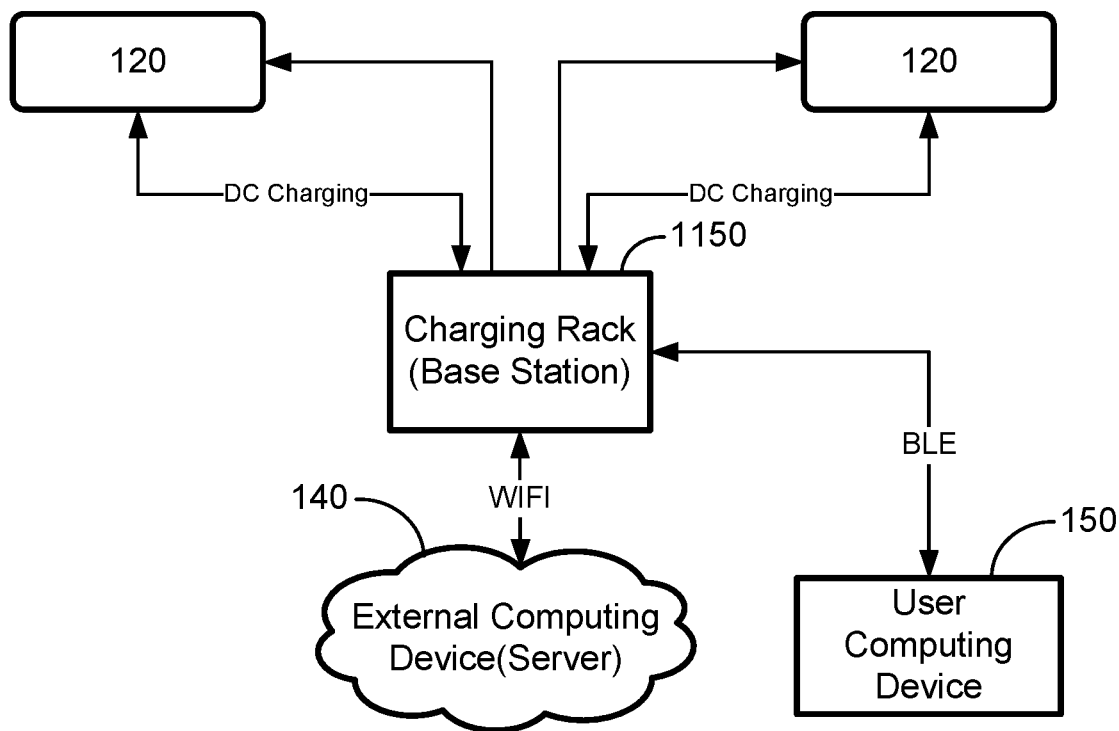
FIG. 12A is a block diagram showing a direct current (DC) charging system of the insole layer of FIG. 4A, according to certain aspects of the present disclosure.

FIG. 12A is a block diagram of the DC charging system for the insole layer 120. One or more insole layers 120 can be positioned on the charging rack 1150 such that DC current can charge the power supply device 438 through the charging socket 433. In the non-limiting example of FIG. 12A, the charging rack 1150 includes more than one DC charging station 1220 (FIG. 12B), each of which is configured to be coupled to the insole layer 120 through one or more magnetic attachments 555. The charging rack 1150 is also wirelessly connected to the external computing device 140 (e.g., by a wireless internet connection) 140 and to the user computing device 150 (e.g., by a Bluetooth Low Energy (BLE) connection). This enables the insole layer 120 to upload motion data generated by the sensors, while the power supply device 438 is recharging.

Figure 12B:
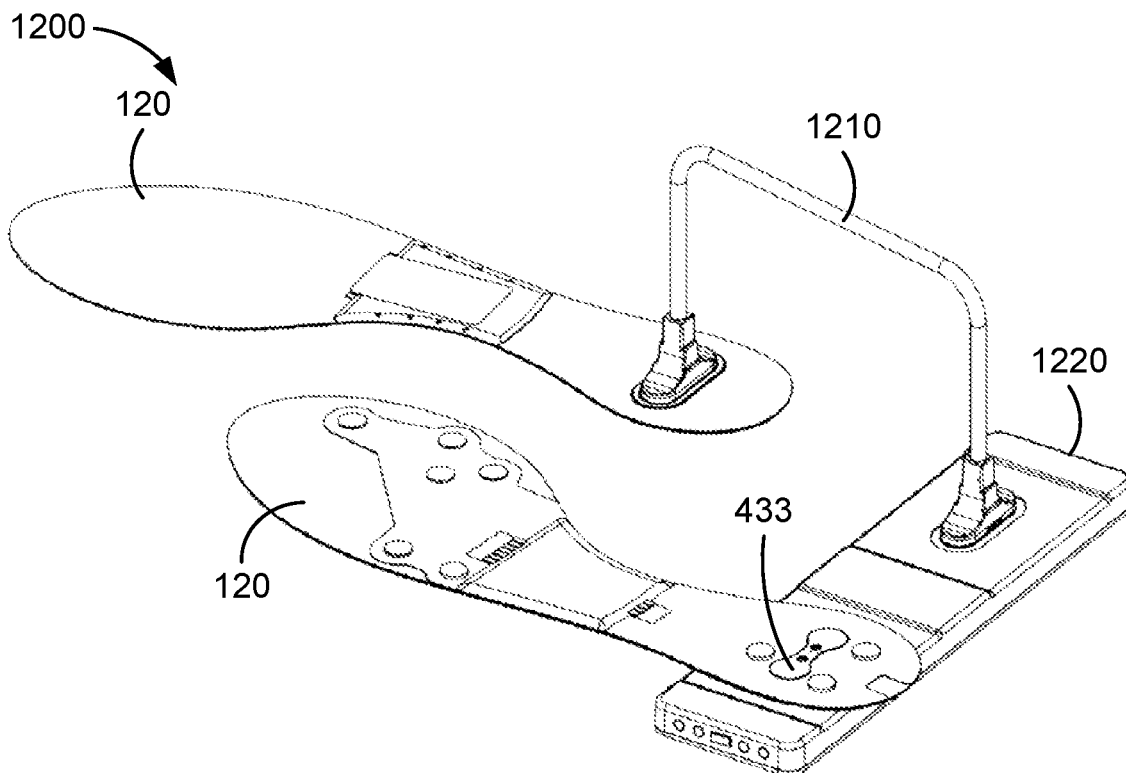
FIG. 12B is a top perspective view showing a DC charging apparatus including a DC charging station for charging the insole layer of FIG. 4A, according to certain aspects of the present disclosure.

FIG. 12B is a top perspective view showing a DC charging apparatus 1200 including a DC charging station 1220 for charging the insole layer 120. As shown in FIG. 12B, the insole layer 120 can be charged by direct contact (e.g., through the magnetic attachments 555) to the DC charging station 1220 or by a charging cable 1210 that connects a DC outlet 1225 (shown in FIG. 12C) of the DC charging station 1220 to the charging socket 433 of the insole layer 120.

Figure 12C:
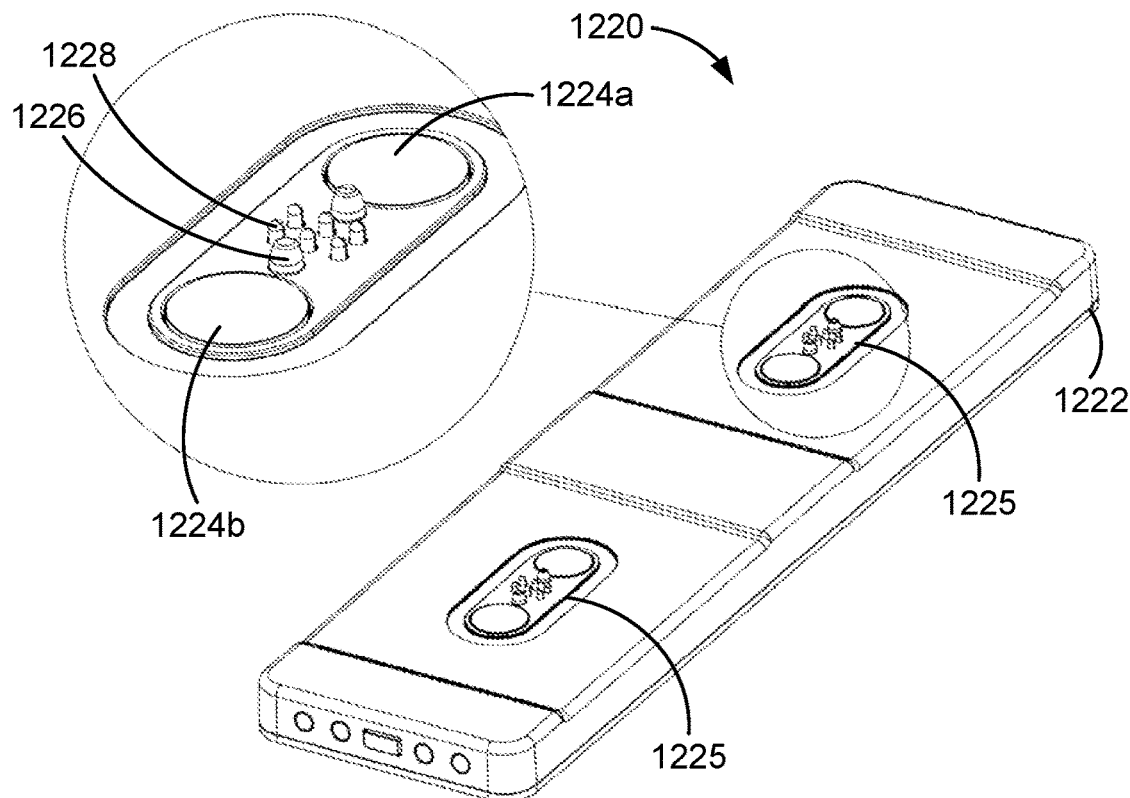
FIG. 12C is a top perspective view of the DC charging station of FIG. 12B, according to certain aspects of the present disclosure.

FIG. 12C is a top perspective view of the DC charging station 1220. The DC charging station 1220 includes two DC outlets 1225 within a housing 1222. As shown in the inlet of FIG. 12C, each DC outlet 1225 includes a magnetic attachment of first polarity 1224a and a magnetic attachment of second polarity 1224b that are configured to be secured to the attachment bracket 550 of the insole layer 120. Each DC outlet 1225 further includes guide pins 1226 and spring-loaded connection pins 1228 for delivering DC current to the insole layer 120, while the insole layer 120 remains secured by the magnetic attachments 1224a, 1224b, The guide pins 1226 are configured to be accommodated through the holes 620 on the flexible PCB 430, shown in FIG. 6A. The spring-loaded connection pins 1228 are configured to be accommodated through the conductive surfaces/traces 630 on the flexible PCB 430, as shown in FIG. 6A.

Figure 12D:
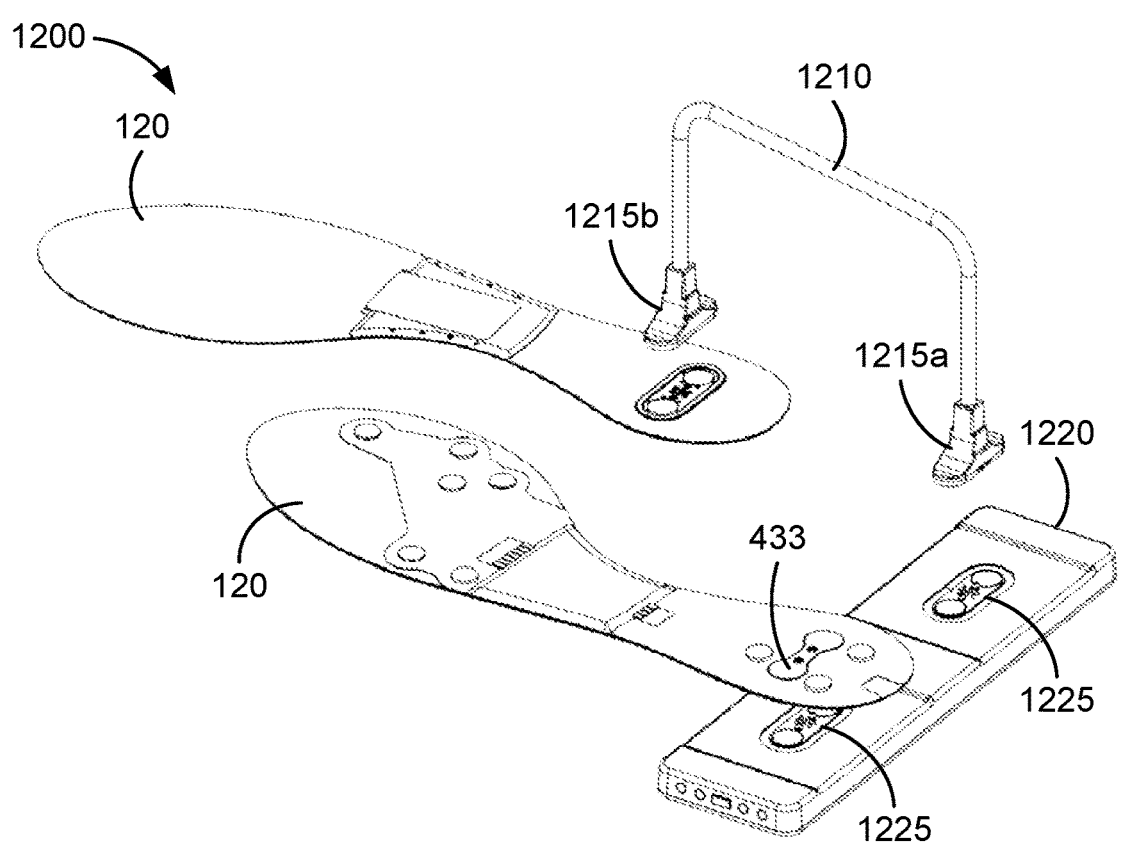
FIG. 12D is a top perspective exploded view showing the DC charging apparatus of FIG. 12B, according to certain aspects of the present disclosure.

FIG. 12D is a top perspective exploded view showing the DC charging apparatus 1200. When the insole layer 120 is charged using the charging cable 1210, a female connector 1215a of the charging cable 1210 connects with the DC outlet 1225 on the DC charging station 1220, while a male connector 1215b of the charging cable 1210 connects with the charging socket 433 on the flexible PCB 430 of the insole layer 120. On the other hand, when the insole layer 120 is charged wirelessly, the charging socket 433 adjacent to the top cover layer 410 (FIGS. 4A-4D) is placed directly over the DC outlet 1225, and the charging socket frame 437 adjacent to the bottom cover layer 420 remains viewable.

Figure 12E:
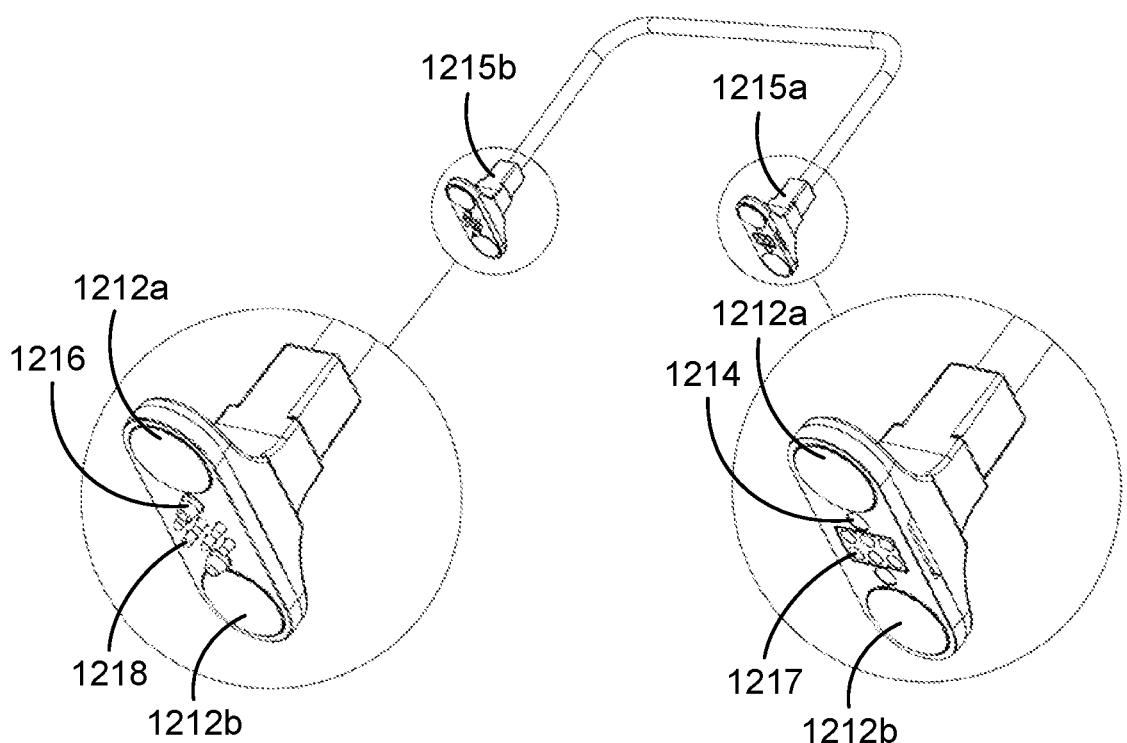
FIG. 12E is a perspective view showing a charging cable of the DC charging apparatus of FIG. 12B, according to certain aspects of the present disclosure.

FIG. 12E is a perspective view showing the charging cable 1210 of the DC charging apparatus 1200. The female connector 1215a of the charging cable 1210 includes a magnetic attachment of first polarity 1212a and a magnetic attachment of second polarity 1212b that are configured to be secured to the magnetic attachments 1224a and 1224b, respectively, of the DC outlet 1225. The female connector 1215a further includes one or more holes 1214 for accommodating guide pins 1226 of the DC outlet 1225, and one or more conductive surfaces/traces 1217 for accommodating spring-loaded connection pins 1228 of the DC outlet 1225.

The male connector 1215b of the charging cable 1210 includes a magnetic attachment of first polarity 1212a and a magnetic attachment of second polarity 1212b that are configured to be secured to the attachment bracket 550 of the insole layer 120. The male connector 1215b further includes guide pins 1216 and spring-loaded connection pins 1218 for delivering DC current to the insole layer 120, while the insole layer 120 remains secured by the magnetic attachments 1212a, 1212b, The guide pins 1216 are configured to be accommodated through the holes 620 on the flexible PCB 430, shown in FIG. 6A. The spring-loaded connection pins 1218 are configured to be accommodated through the conductive surfaces/traces 630 on the flexible PCB 430, as shown in FIG. 6A.

As noted above, the power supply device 438 of the insole layer 120 can be charged using either the wireless RF charging system shown in FIG. 11A, the DC charging system shown in FIG. 12A, or the both. Once the power supply device 438 is fully charged, the insole layer 120 remains dormant until one or more sensors, such as the force-sensitive resistors, the three-axis accelerometers, and the three-axis gyroscopes detect movement over a predetermined threshold value. Thus, the insole layer 120 becomes active only when the insole layer 120 detects a full body weight, resultant ground reaction forces being exerted, movement, and/or a change in direction. At that point, the sensors in the insole layer 120 begin collecting motion data of the user as a new session or a predesignated session. A session may be defined as a period of time where a user is involved in physical activity such as a training session, a clinical session, or open play such as a match. The session may be verified through other records of the session, which may be correlated with the data record. The session and data collection may be paused if the insole layer detects no movement for about 60-120 seconds, and then resumes as soon as movement is detected. The session ends when the insole layer 120 or footwear (e.g., a shoe, or the sock 110) is placed on the charging rack 1150.

During a session, the combined data generated from the insole layer 120 is encrypted and uploaded in real-time via the router device 534. In some embodiments, the encrypted data is automatically stored, processed and shared, on an open data-driven and permissioned block chain 170. This provides a traceable, timestamped record of motion data from different sessions (e.g., from training, clinics, open play) that cannot be deleted or falsified. As a result, motion data of the user can become a living historical record, which can be accessed and shared with different parties (e.g., medical provider, employer, family, coach) in a controlled fashion.

Figure 13:
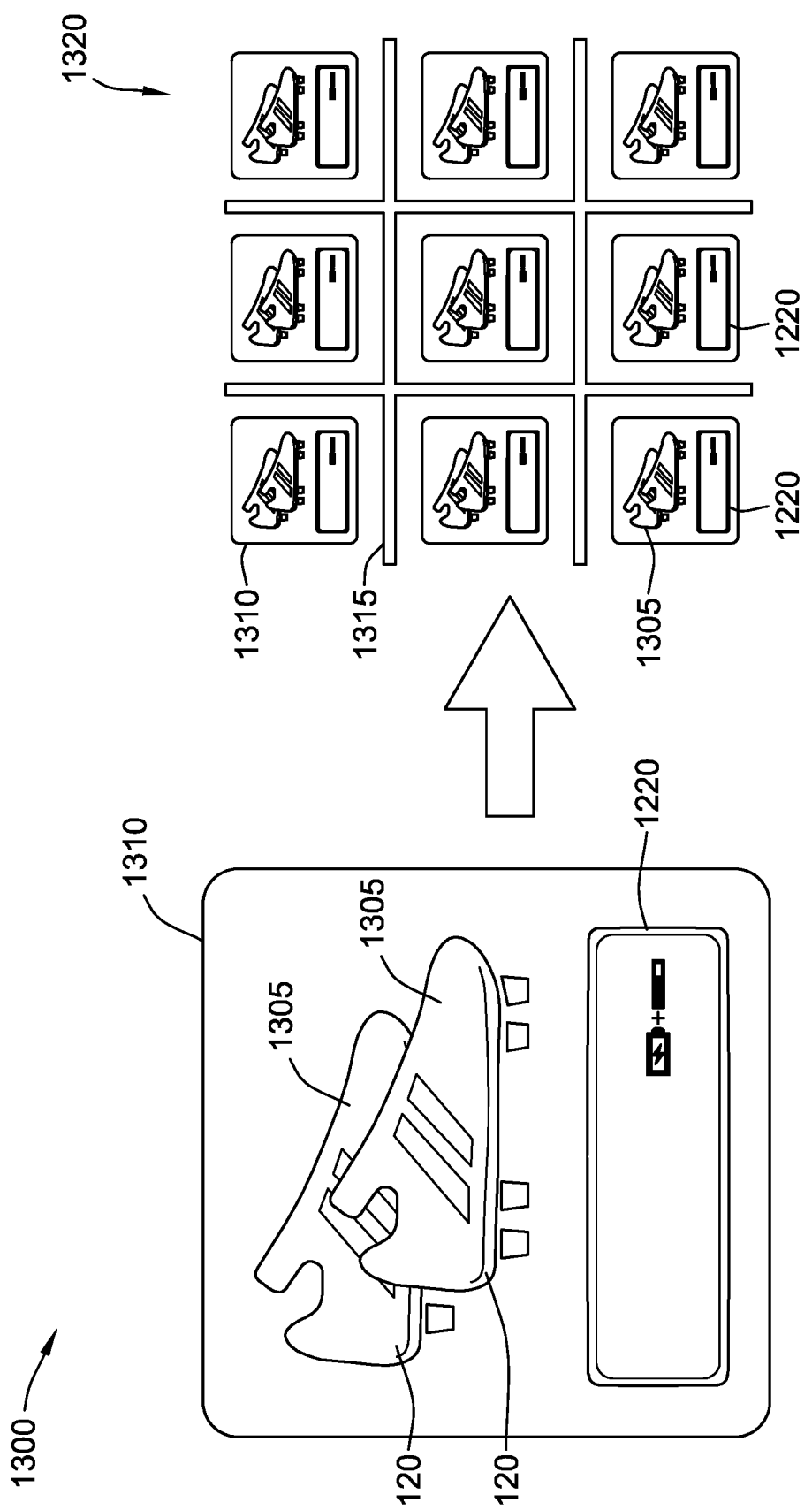
FIG. 13 is a schematic representation of charging the insole layer of FIG. 4A on a stationary rack module, according to certain aspects of the present disclosure.
Figure 14:
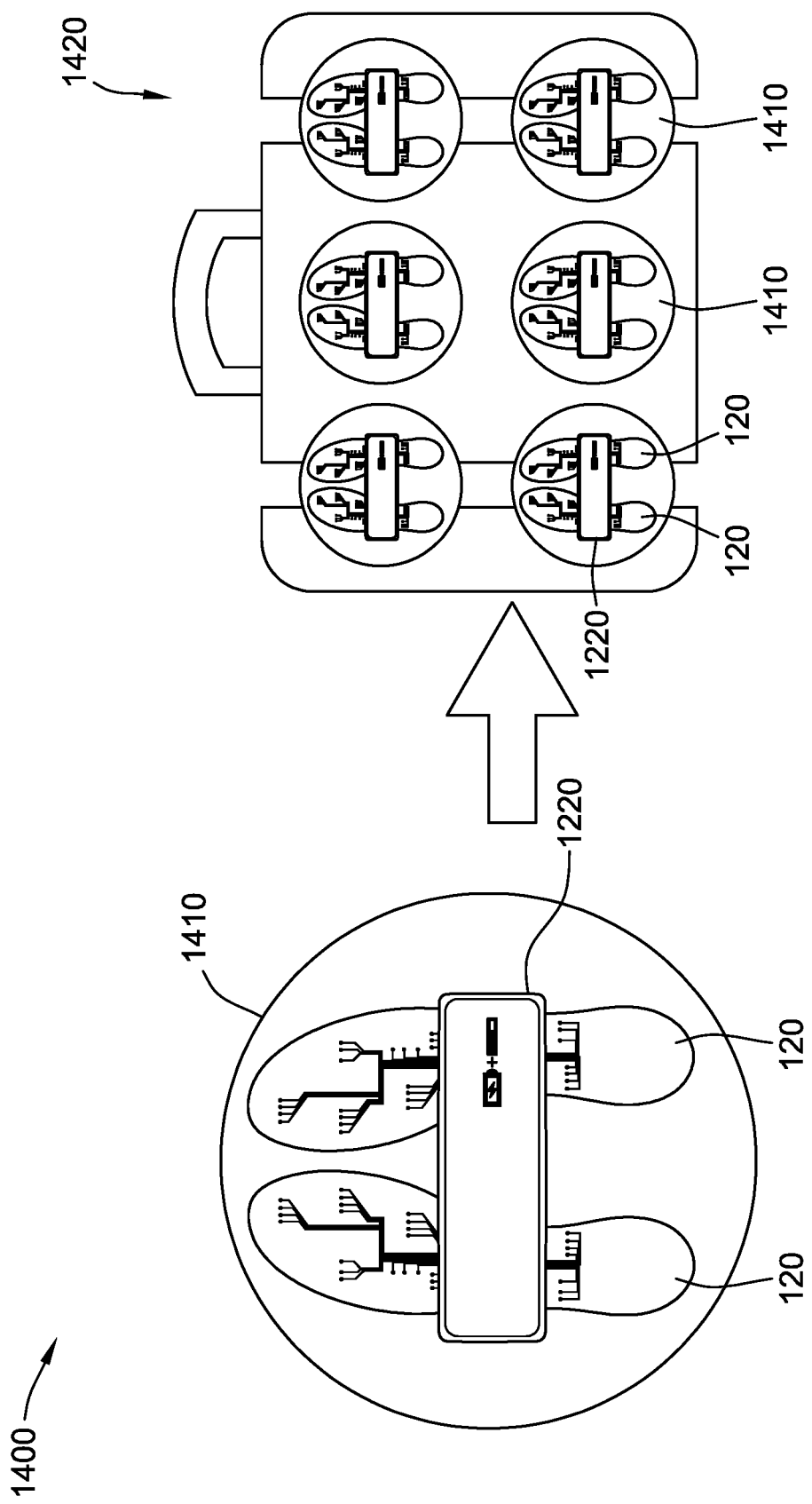
FIG. 14 is a schematic representation of charging the insole layer of FIG. 4A on a portable sleeve module, according to certain aspects of the present disclosure.

The power supply device 438 of the insole layer 120 can be charged using the DC charging station 1220, which can be a stationary rack module 1310 (shown in FIG. 13) or a portable sleeve module 1410 (shown in FIG. 14). FIG. 13 is a schematic representation of the process of charging the insole layer 120 using the stationary rack module 1310. Each stationary rack module 1310 includes a DC charging station 1220, on which the insole layer 120 or shoes 1305 with the insole layer 120 can be placed for charging. Multiple stationary rack modules 1310 can be placed on racks 1315 of a DC charging shelf 1320, which can be used by many users simultaneously for charging the insole layer 120.

FIG. 14 is a schematic representation of the process of charging the insole layer 120 using the portable sleeve module 1410. Each portable sleeve module 1410 is made of a foldable technical fabric such as, but not limited to, Acrylonitrile Butadiene Styrene (ABS), High-Impact Polystyrene (HIPS), High-Density Polyethylene (HDPE), Polyvinyl Chloride (PVC), Polyethylene Terephthalate (PET), Thermoplastic Polyolefin (TPO), and the like. Each portable sleeve module 1410 can have one or more DC charging stations 1220, on which the insole layer 120 can be charged. Multiple portable sleeve modules 1410 can be placed on travel case 1420 for use during travel. In some embodiments, the travel case 1420 itself can be recharged through an independent power connection to a 12V power supply.

The systems and methods of monitoring human lower limb and foot performance as described herein can be configured to provide time-stamped prescriptive and augmented analytics of the motion data generated from the sock 110, the insole layer 120, and any wearable device connected to them.

The motion data is analyzed to determine three categories of metrics—load, force distribution, and gait using a load module, a force distribution module, and a gait module respectively in software executed by the processor 142, the processor 312, and/or the processor 536. The load module calculates the force imparted to each insole layer 132 across the sensing areas 435 during the session, while each foot is in contact with the ground. Using a threshold-based algorithm and using both the force-sensitive resistor and inertial sensors described above, the load module determines both the initial contact (IC) and final contact (FC) points of the foot with the ground during the gait cycle.

The force-sensitive resistors capture raw pressure data from each of the sensing areas 435 and transforms it into force data, via a force calibration algorithm. The force calibration algorithm approximates the ground reaction force during a gait from the motion data generated by the insole layer. The force calibration algorithm is trained by data captured from a variety of subjects and forms of footwear under a variety of stepping conditions using a piezo-electric force plate.

The inertial sensors add more granularity to high-impact forces experienced by the user during IC with the ground during running and jumping motions. The load module uses both IC and FC points to provide temporal boundaries for subsequent calculations. The load metrics are determined through the output of the force calibration algorithm and analyzed by a subject matter expert, which provides the user with mechanical load data from the interaction of the foot with the ground.

As a non-limiting example, load data is obtained from a group of athletes wearing insole layers 120 following a training session. Load data maybe collected hourly or daily, and used to calculate weekly, monthly and season load totals. This is termed 'longitudinal load monitoring'. Athletes are monitored consistently, with special attention made to those who are recovering from injury, or have recently recovered from injury. Cumulative load 'budgets' are utilized to control the amount of load each athlete is subjected to during training and competing, over a given period of time. When athletes are at risk of exceeding their load 'budget' due to a training session exhibiting more load than planned/expected, subsequent training sessions can be modified in order to keep an athlete within their 'budget' and thereby mitigate the risk of injury.

The force distribution module uses calibrated force data to calculate the force differences between left and right foot, as well as the differences between the various regions of each foot. Through the subject matter expert, force-sensitive resistors in the insole layer 120 captures data from the most relevant regions of the foot, providing insight into the loading pattern experienced by the user during the gait cycle. The regions of the foot are separated into rearfoot (heel), midfoot (middle) and forefoot (toward toes) to simplify insight and facilitate understanding. The characteristics of regional load distribution are presented to the user in simple terms to provide an objective measure of symmetry between left and right sides, as well as regions of each foot. The symmetry calculation is based on either force or impulse. One example of a symmetry calculation is a ratio between a difference and a sum of the measurements of the left foot and the right foot.

As a non-limiting example, force distribution data is obtained from a group of athletes wearing the insole layers 120 following a training session. The data provides insight into the symmetry of movement of each athlete throughout the training session (i.e. the difference in load taken through the left and right foot). Symmetry data is collated longitudinally, allowing comparison between the data from a single training session and an athlete's 'symmetry average' over a period of time. When a particular athlete is found to have exhibited a symmetry measurement from a training session that differs significantly from their 'symmetry average', the athlete can be screened by medical staff to detect whether a new injury, or functional deficit, may be responsible for the change in symmetry. In this way, 'at risk' athletes can be screened following training, facilitating the application of corrective exercises or manual treatment, thereby mitigating the risk of injury resulting from subsequent training sessions The gait module uses both IC/FC points and calibrated force/impulse data to calculate metrics that provide more detailed insight into the gait strategy used by each user. This is higher-level information designed for use by the user or an experienced medical or athletic coach looking to understand the unique movements involved during the gait cycle, determine normal gait patterns for a given footwear/ground interface, diagnose issues causing pain and implement effective corrective exercise or treatment to correct abnormalities. Gait metrics can be separated into temporal, spatial, kinetic and kinematic categories.

The gait module includes temporal metrics (based on time) that include, but are not limited to, contact time (time in which one foot is in contact with the ground), flight time (time in which neither foot is in contact with the ground during running), dual-support time (time in which both feet are in contact with the ground during walking), swing time (duration of the swing phase of the gait cycle), and duty factor (the ratio of contact time to the sum of contact and flight times, which is a measure of efficiency). Other temporal gait metrics include step frequency (number of steps per second or minute) and stride frequency (numbers of complete strides per second or minute).

Spatial gait metrics include, but are not limited to, step length (distance covered during one step) and stride length (distance covered during one stride). Both of these metrics involve a calculation of speed which may be derived by a supervised machine learning process involving motion data captured by both the force-sensitive resistors and the inertial sensors described above.

Kinetic gait metrics include peak and average forces in either the vertical, frontal or lateral plane, as well as representation of force angle and gait line (the path of force throughout the foot), derived from the force calibration algorithm previously discussed.

Kinematic gait metrics include distance covered, movement speed, swing leg velocity, acceleration, and are all dependent on the modelling of speed from the sensor data.

As a non-limiting example, gait data is obtained from an athlete wearing tech layers following a rehabilitation training session. The rehabilitation process can be informed in detail by utilizing gait metrics to understand the strategies employed by an athlete to execute a movement task. Throughout a rehabilitation period, following long-term injury or surgery, gait metrics can be used by the experienced practitioner to guide the progression of exercises they apply to the athlete. By comparing the gait metrics collected during a task that is performed post-injury with 'baseline' gait metrics collected when performing the same task pre-injury, the practitioner is provided a means to assess an athlete's readiness for the task. In this example, use of gait data by a skilled practitioner, can significantly increase the likelihood of a successful rehabilitation period, enabling an athlete to safely return to the field of play in the shortest possible time.

The prescriptive and augmented analytics may be viewed as interactive visualizations on a software application interface on the display 156 of the user computing device 150. The software application may be used before, during, or after a session for a single athlete, or group of athletes. The software application is also used to mark one or more periods within a session, providing a means for the user to separate a session into meaningful portions and/or determine analytics based on any combination of the sensors, thereby enriching the insights available following analysis and the interactive visualizations based on the motion data. The software application may be used to capture and record video data corresponding to one or more periods of the session during which motion data is collected to facilitate a greater understanding of the motion data over time. The software application can also be used to switch collection of motion data between a "live" mode for livestreaming the motion data captured by the sensors during a session, and a "recall" mode for viewing recorded motion data associated with one or more periods of the session, which may be user-selected. This provides the user with information in real-time during a session and after a session, which generate insights into the 'athlete load', performance, and risk of injury. Further, the software application may provide the ability to overlay forces on the left foot and the right foot on a time base from the captured recording or livestream, visualize the data in different areas of the foot—sum the individual loads on the heel area, the lateral area, the medial area and the forefoot area on each insole layer 120, or sum each of the entire insole layers on the left foot and the right foot, as well as related analytics such as average force, peak force, cumulative force, percent symmetry between left foot and right foot, contact time, flight time, etc.

The interactive visualizations can occur both in real-time as well as a recorded feed after a session has been completed. In some embodiments, the interactive visualizations include motion graphics with force-time series data streamlined in real time. In some embodiments, the analytics may include average force, peak force, cumulative force, force-frequency profile, muscle activation level, contact time, etc. for different areas of each foot and leg, as selected by the user. Further, the analytics may include interplay between the different legs and feet such as, but not limited to, percent loading symmetry between left foot and right foot.

Individual motion data sets from each of the sensors and wearable devices described above may be viewed separately or cumulatively, and combined with a video recording of the motion to gain in-depth insight into the movement of the user. An indication may be delivered when there is a threshold percentage change from base line values that suggest overloading or if overloading is being avoided.

Figure 15:
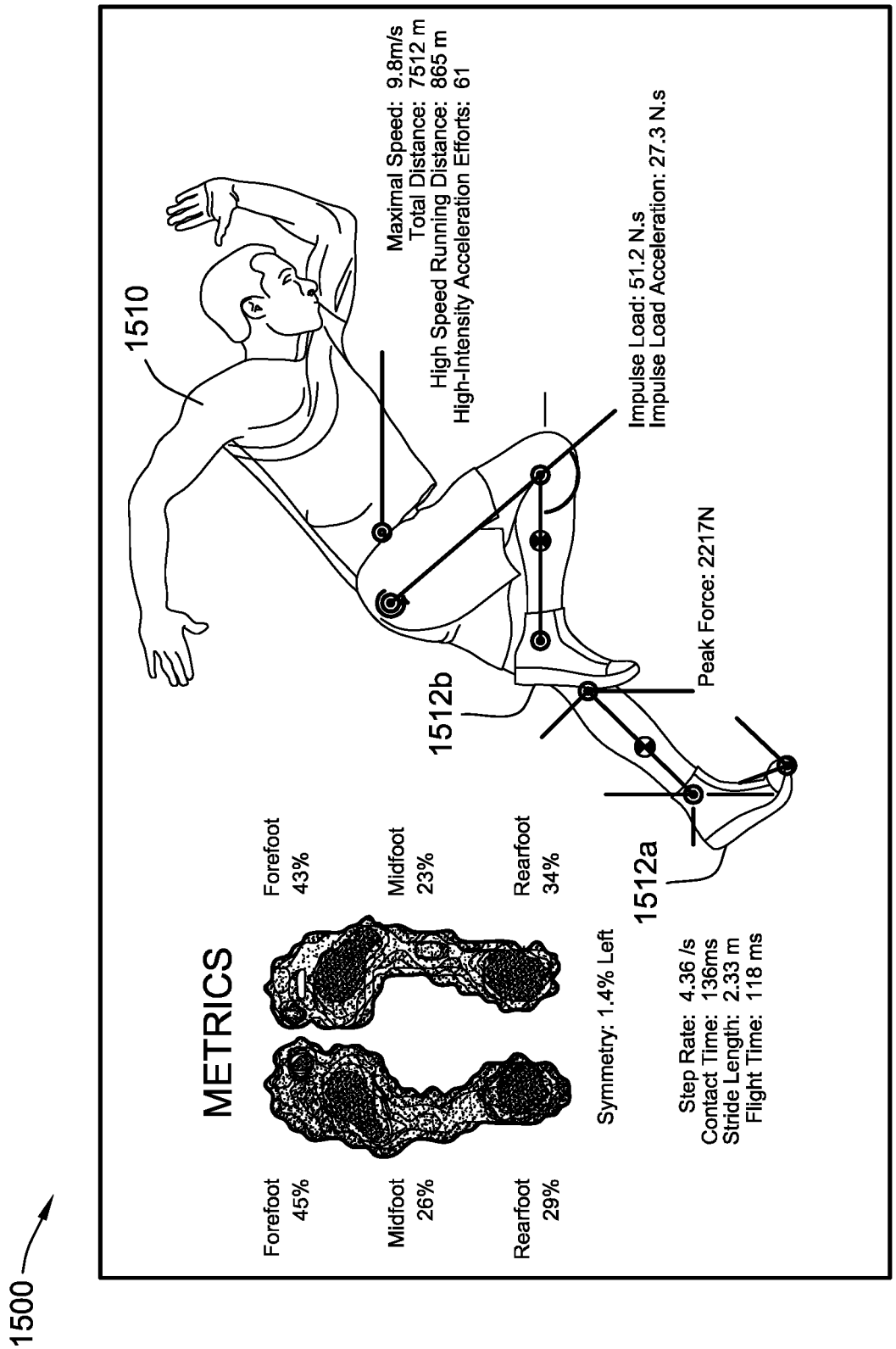
FIG. 15 shows an interactive visualization related to motion of a user on a first embodiment of a software application interface, according to certain aspects of the present disclosure.

FIG. 15 shows a non-limiting example of an interactive visualization 1500 related to motion of a user 1510 on a first embodiment of a software application interface. The visualization 1500 includes metrics derived from motion data collected by the insole layer 120 worn by the user 1510. The metrics may include a heat map of loading in different areas of the left foot 1512a and the right foot 1512b of the user 1510, and gait features such as step rate, contact time, stride length, and flight time. The visualization 1500 further includes motion characteristics such as speed, acceleration, impulse, as well as, delineation of different loads on the left foot 1512a and the right foot 1512b.

Figure 16A:
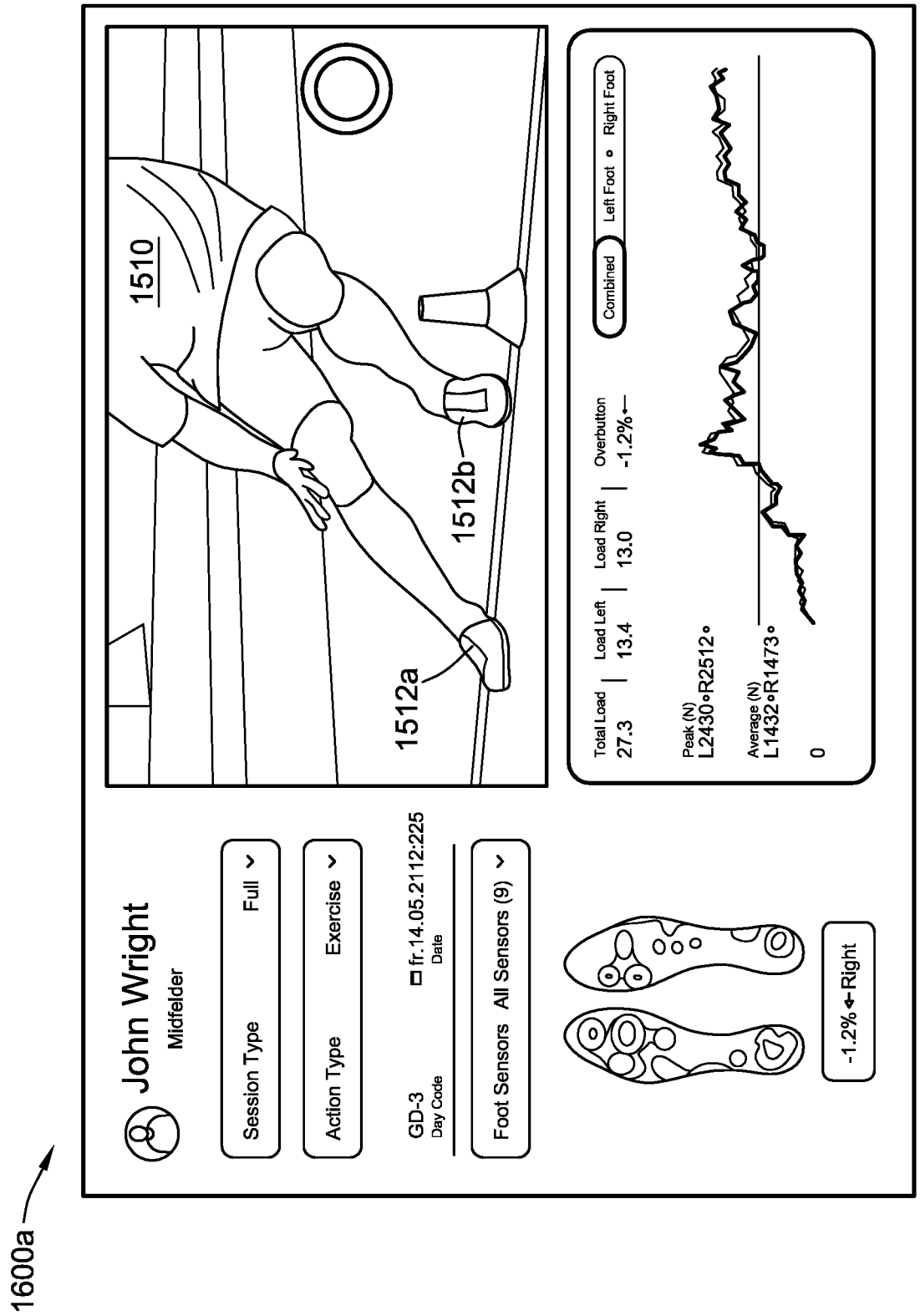
FIG. 16A shows a first interactive visualization related to motion of the user on a second embodiment of the software application interface, according to certain aspects of the present disclosure.
Figure 16B:
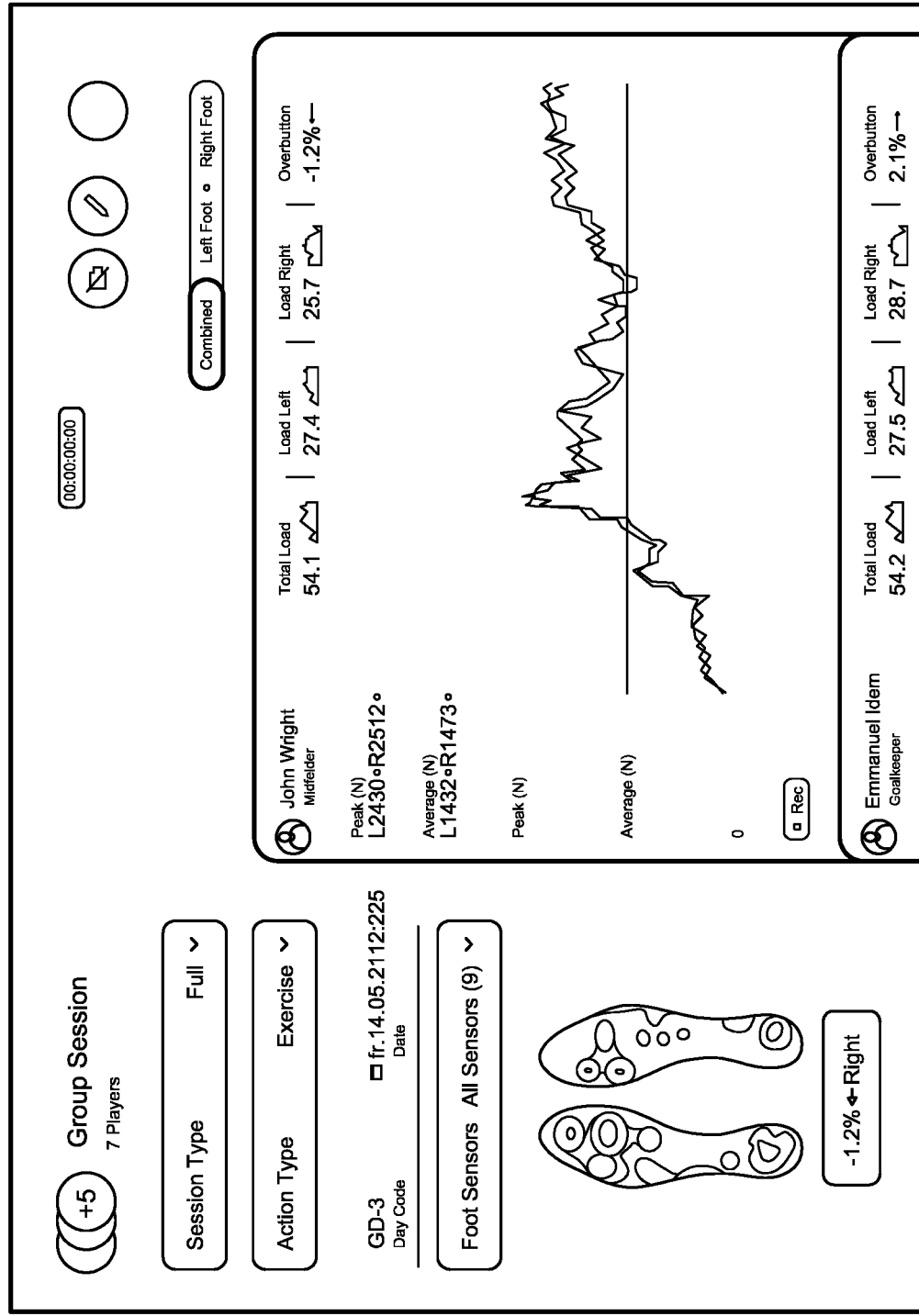
FIG. 16B shows a second interactive visualization related to motion of the user on the second embodiment of the software application interface, according to certain aspects of the present disclosure.

FIGS. 16A-16B show non-limiting examples of a first interactive visualization 1600a and a second interactive visualization 1600b, respectively, on a second embodiment of the software application interface. The first interactive visualization 1600a shows live or recorded information on load applied on the left foot 1512a and the right foot 1512b of the user 1510, determined from all sensors of the insole layer 120 during an individual exercise session on a certain day. The visualization 1600a includes a heat map showing percent loading symmetry between the left foot and the right foot for the user, and a graphical plot of peak force and average force on the on the left foot 1512a and the right foot 1512b of the user 1510. The visualization 1600a can be interacted to alter the presentation of the motion data such, but not limited to, viewing motion data for only the left foot 1512a or only the right foot 1512b, viewing motion data from only a selection of the sensors, etc.

The second interactive visualization 1600b shows live or recorded information on load applied on the left foot and the right foot of each of seven users, determined from all sensors of the insole layer 120 by each of the users during a group exercise session on a certain day. The visualization 1600b presents individual heat maps showing percent loading symmetry between the left foot and the right foot for each of the seven users, and a graphical plot of peak force and average force on the left foot and the right foot of the each of the seven users. The visualization 1600b can be interacted to alter the presentation of the motion data such, but not limited to, viewing motion data for only the left foot 1512a or only the right foot 1512b, viewing motion data from only a selection of the users, sessions, or sensors, etc.

Figure 17:
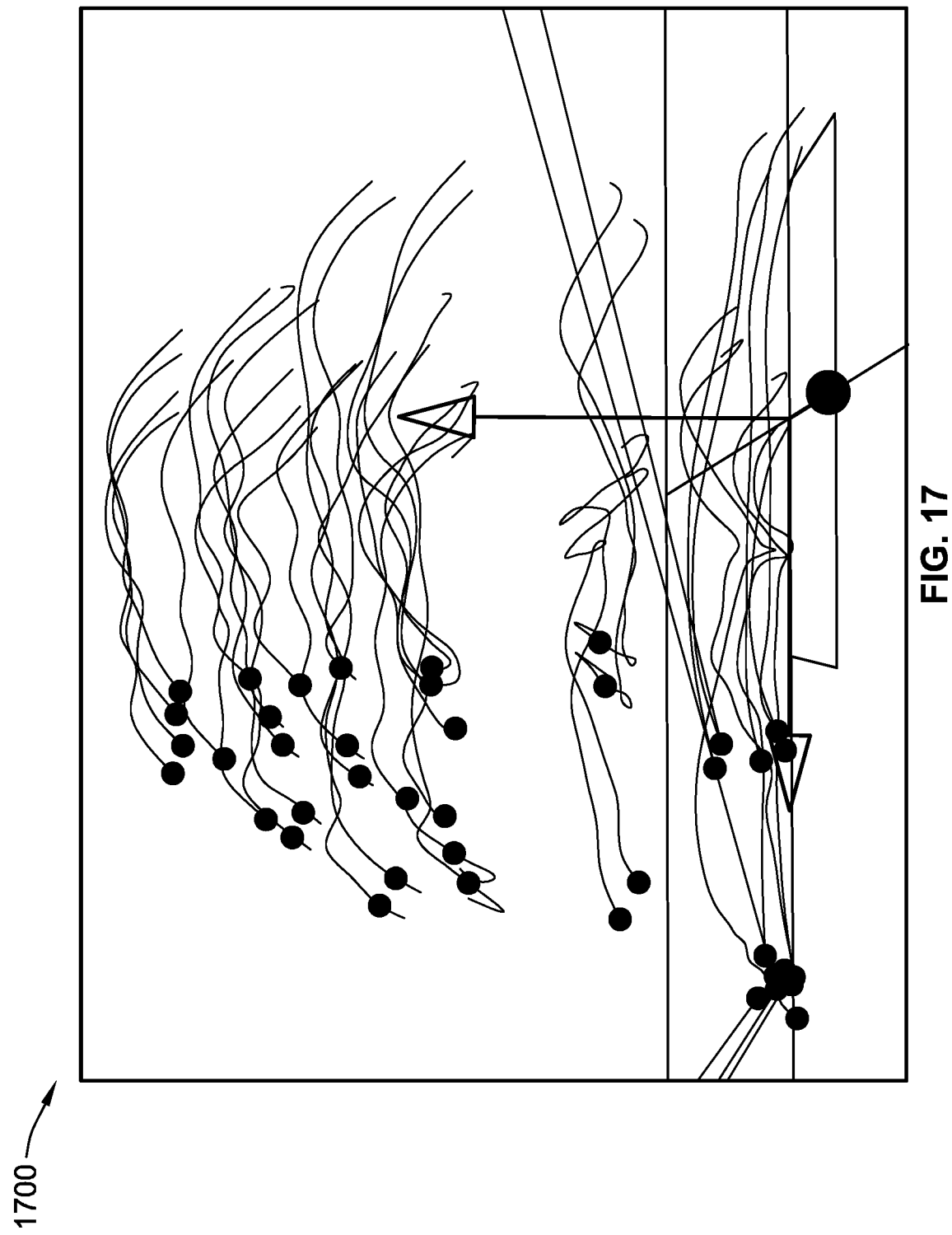
FIG. 17 shows a three-dimensional skeletal output graph representing motion of the user on a third embodiment of the software application interface, according to certain aspects of the present disclosure.

FIG. 17 shows a three-dimensional skeletal output graph 1700 representing motion of a user on a third embodiment of the software application interface. The three-dimensional skeletal output graph 1700 plots load distribution over time of individual sensing areas on the feet of the user over time during a session using one or more of the sensors described above.

Figure 18A:
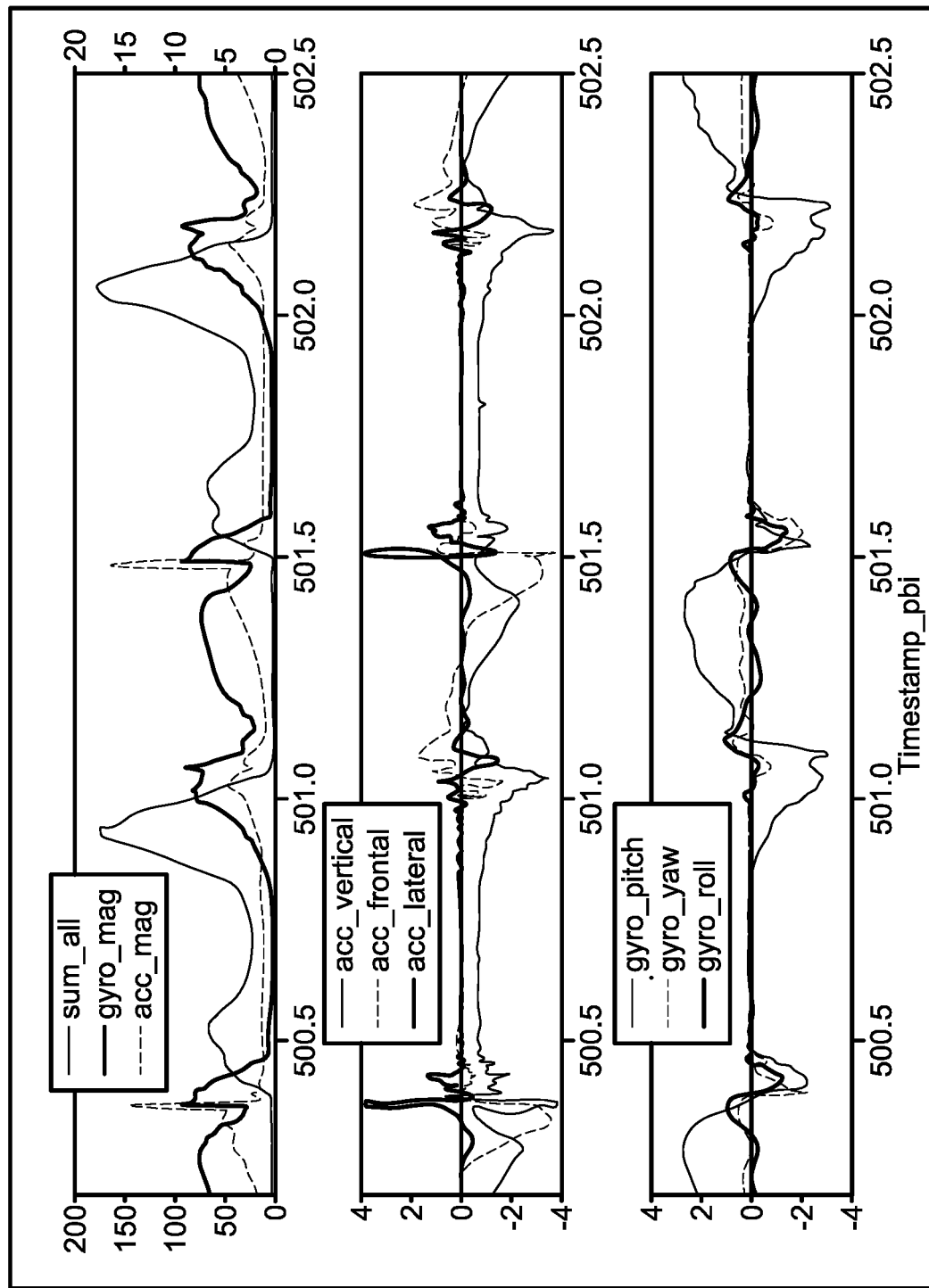
FIG. 18A shows a first interactive visualization related to motion of the user on a fourth embodiment of the software application interface, according to certain aspects of the present disclosure.
Figure 18B:
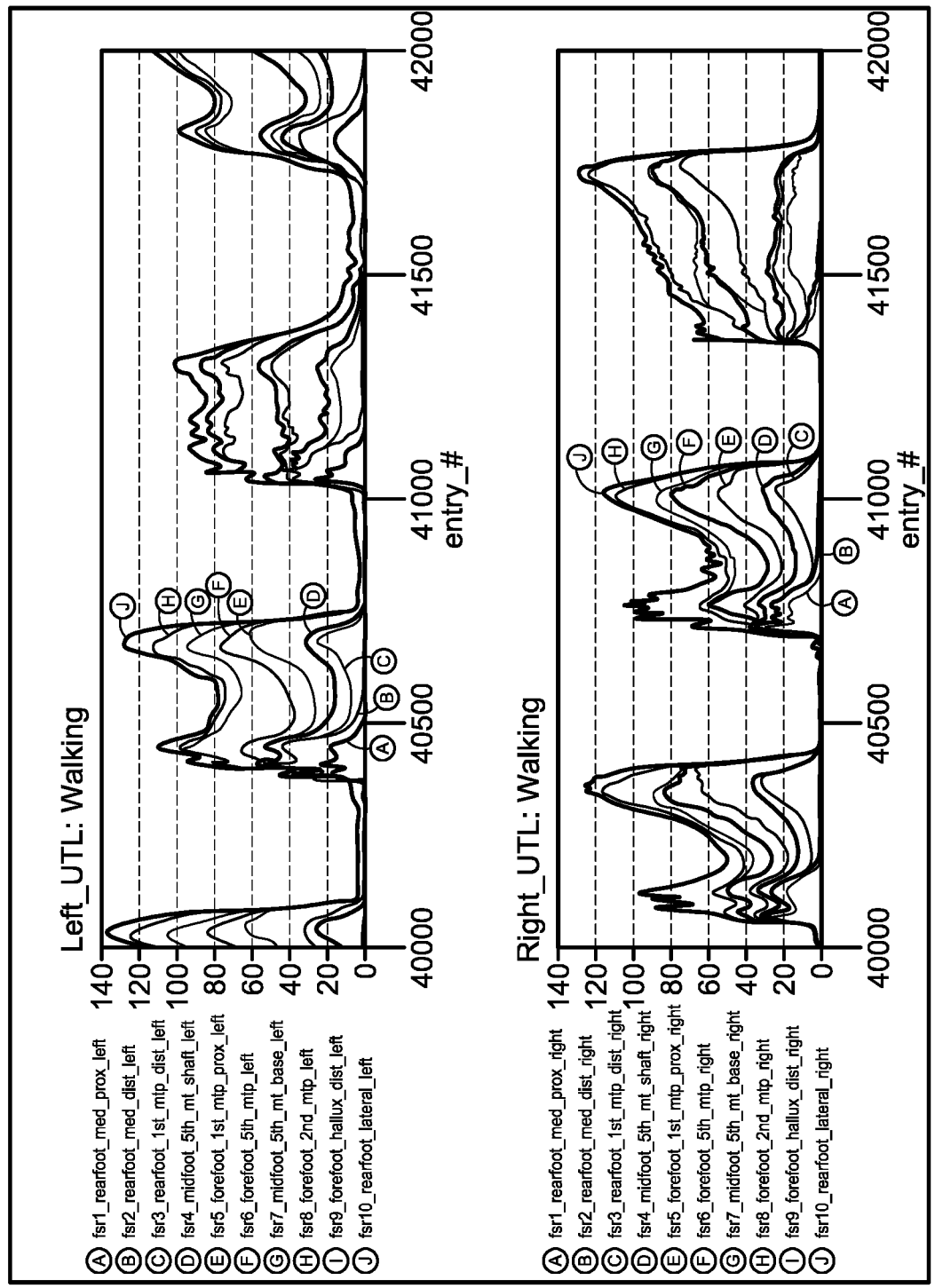
FIG. 18B shows a second interactive visualization related to motion of the user on the fourth embodiment of the software application interface, according to certain aspects of the present disclosure.

FIGS. 18A-18B show non-limiting examples of a first visualization 1800a and a second visualization 1800b, respectively, on a fourth embodiment of the software application interface. The motion data in the visualizations 1800a and 1800b may be collected from the insole layer 120. The visualization 1800a shows a comparative graphical plot of translational displacement in three directions over time obtained from a three-axis accelerometer of the insole layer 120, rotational displacement in three directions over time obtained from a three-axis gyroscope of the insole layer 120, as well as magnitude of net translational and rotational displacements of the foot of the user over time. The visualization 1800b shows a comparative graphical plot of load distribution over time measured by individual force-sensitive resistors in each region of the left foot and right foot of a user during a walking session.

Figure 19:
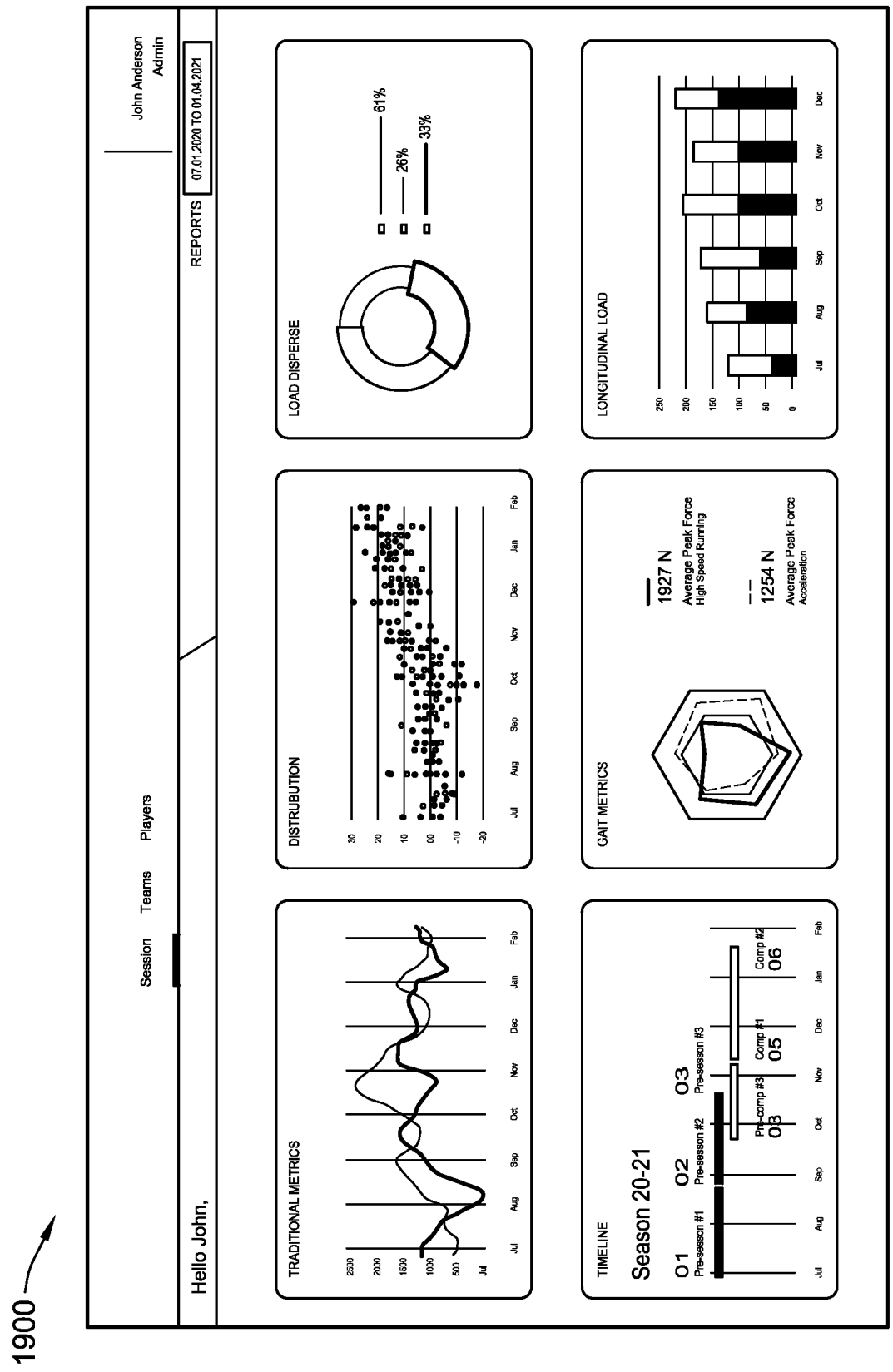
FIG. 19 shows an interactive visualization related to motion of a user on a fifth embodiment of the software application interface, according to certain aspects of the present disclosure.

FIG. 19 shows a non-limiting example of an interactive visualization 1900 related to motion of a user on a fifth embodiment of the software application interface. The data in the visualization 1900 may be collected from the insole layer 120. The interactive visualization 1900 presents a number of selectable analytical insights. The insights may include such as traditional metrics, load distribution on a foot over sessions over a period of time (e.g., six months), load dispersal, timeline of sessions from which data was collected, metrics of gait features like peak force, and longitudinal load experienced by the user. Any one of the analytical insights can be selected and then viewed for individual sessions, teams, user, and the like. One or more of these analytical insights may be derived from the motion data of the user using one or more machine learning algorithms explained above.

Figure 20:
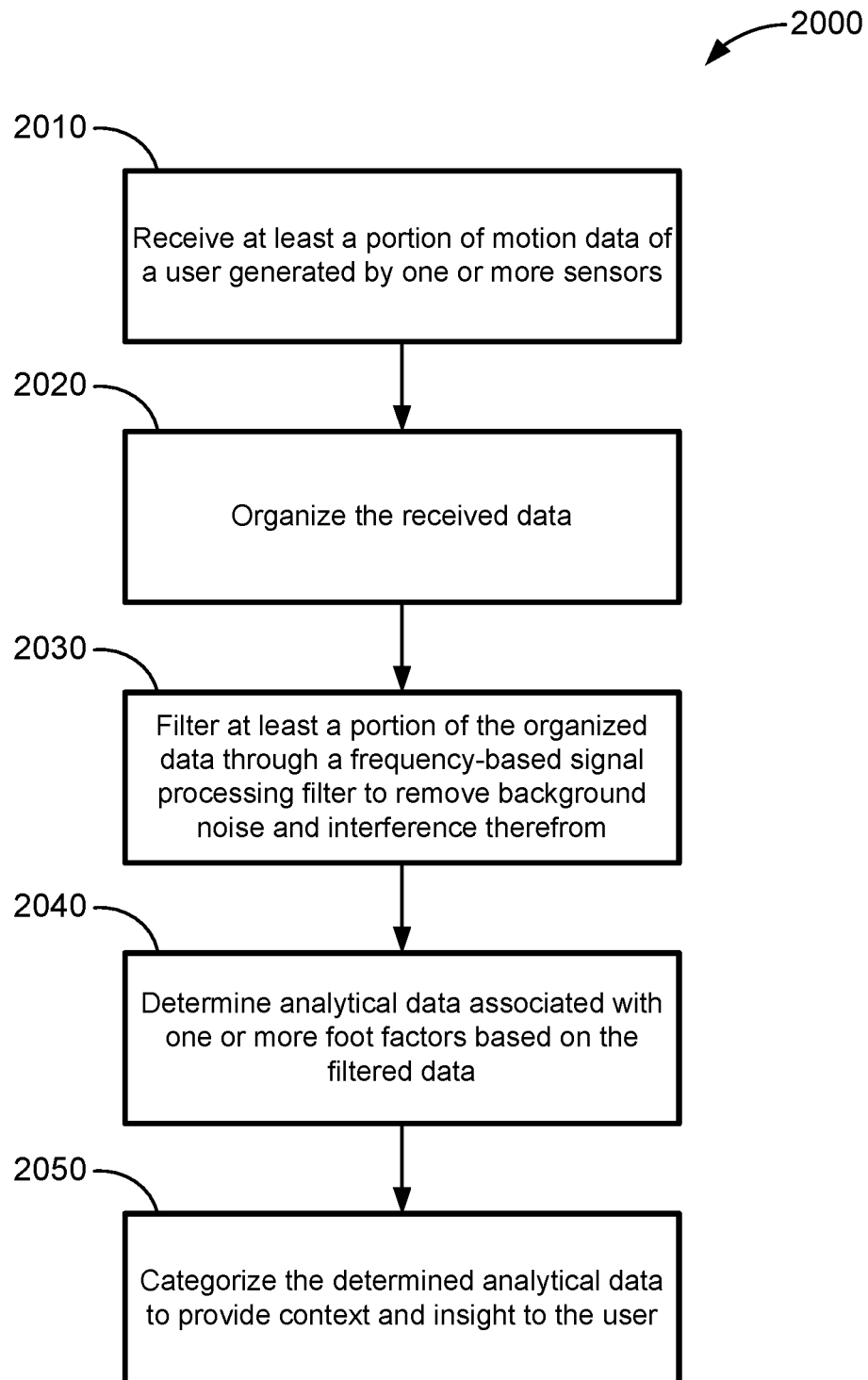
FIG. 20 shows a block diagram of a data analytics method performed by a motion analytics system having the sock of FIGS. 2A-2B and/or the insole layer of FIG. 4A, according to certain aspects of the present disclosure.

FIG. 20 shows a block diagram of a data analytics method 2000 performed by the motion analytics system 100 using motion data generated from the sensors in the sock 110 and/or the insole layer 120 of the user. The sensors may include force-sensitive resistors that measure loading at different pressure points on the foot, three-axis accelerometers that measure translational motion of the foot, gyroscopes that measure rotational motion of the foot, magnetometers that measure change of direction during movement of the foot, temperature sensors for measuring heat-generated due to movement of the foot, electromyography sensors that measure muscle activation and fatigue, and heart sensors that measure and monitor heart health parameters of the user.

The method 2000 begins in block 2010, where at least a portion of the motion data of the user generated by the sensors, is received. The motion data may be received by a processor within the sock, the insole layer, an external computing device, a user computing device, and any device that is capable of further processing and analyzing the motion data.

In block 2020, the received data is organized. In some embodiments, the process of organizing the received data may include assigning user characteristics to the received motion data. The user characteristics may include information about the user such as, but not limited to, age, gender, location, nationality, shoe size, height, weight, surface of interaction of the user's feet, nutritional facts about the user, past injuries, physiological parameters such as heart rate and blood pressure, etc. This data may be collected by a user via an interface presented to the user on a user computing device.

In some embodiments, the process of organizing the received data may include segmenting one or more portions of the received data based on one or more user-defined time-stamped sessions. As an example, the received data can be divided into data acquired during a training session, clinic session, activity session, etc., where each session has a designated time period.

In some embodiments, the process of organizing the received data may further include validating the received motion data through removal of erroneous and missing data, thereby ensuring data integrity. The erroneous and missing data could be due to a dysfunctional sensor, improper capture of data, inaccurate transmission of captured data. Accordingly, it is important to purge erroneous and missing data points from received data to ensure data integrity. The erroneous and missing data may then be interpolated into the validated data to form a consistent and organized data set for further processing and analysis.

In block 2030, at least a portion of the organized data is filtered through a frequency-based signal processing filter to remove background noise and interference therefrom. In some embodiments, the frequency-based signal processing filter may be a Butterworth filter.

In block 2040, analytical data associated with one or more foot factors is determined based on the filtered data. In some embodiments, the foot factors may be a step of the user, a speed of the user, force and impulse of each step of the user, customized features based on the user characteristics, and the like. The analytical data may be determined in a number of ways. In a non-limiting embodiment, the analytical data may be determined by recognizing patterns in the filtered data through a classification algorithm, or a regression algorithm. Additionally or alternatively, the analytical data may be determined by detecting gait features of the user such as, but not limited to, ground contact time of a foot of the user, flight time of the user, a contact time of the foot of the user, a step frequency of the user, a stride length of the user, stride rate of the user, progression line of the user, a foot angle of the user, a gait center of the user, a stepping force of the user, etc.

In block 2050, the determined analytical data is categorized to provide context and insight to the user. In some embodiments, the categorization may be based on a type of motion of the user depending on a speed and acceleration of the user, force and impulse of each step of the user, a directional change of the user, etc. Additionally or alternatively, the determined analytical data is categorized based on a left foot or right foot of the user and the observant symmetry of load distribution and performance between the two. Additionally or alternatively, the determined analytical data is categorized based on dispersion of the data across regions, i.e. front portion, middle portion, and rear portion within a left foot of the user, or a right foot of the user.

In some embodiments, the categorized data is further compiled and presented along with a predictive feedback on the motion of the feet of the user. The predictive feedback is determined by a supervised or an unsupervised machine learning algorithm trained on motion data and resulting outputs. In some embodiments, the predictive feedback may include information related to symmetrical distribution of forces on the feet of the user during motion, likelihood of injury of the user, one or more patterns of injury of the user, a recommended course of action to prevent an injury to the user, and the like. In some embodiments, the predictive feedback may be presented along with interactive visualizations to provide context and insight about the motion data to the user. The motion data, the interactive visualizations, and the predictive feedback may be downloaded or exported in various formats by the user for future use, study, and research.

Figure 21:
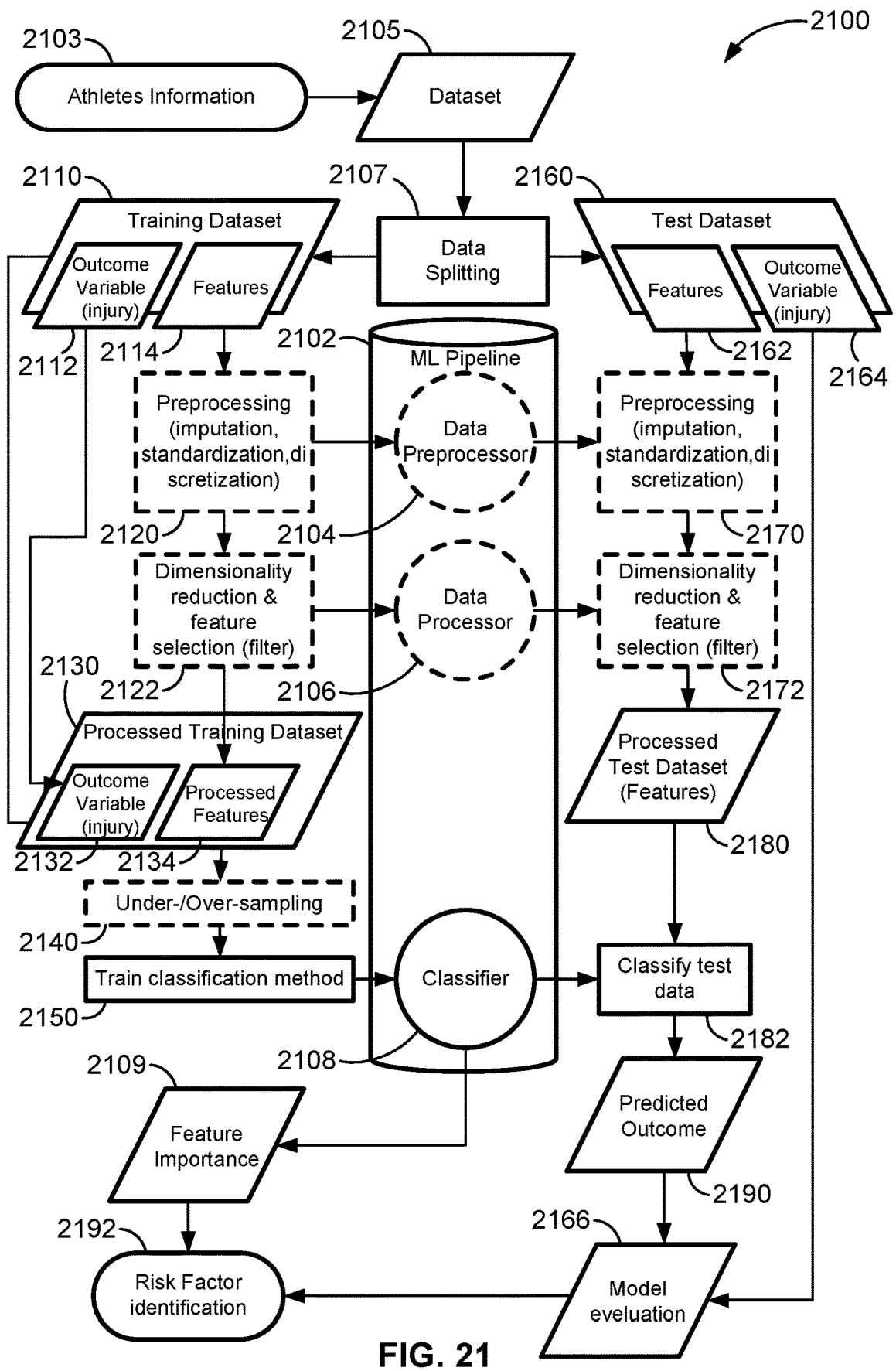
FIG. 21 shows a block diagram of a non-limiting example of a machine-learning architecture used by the data analytics method of FIG. 20, according to certain aspects of the present disclosure.

FIG. 21 shows a block diagram of a non-limiting example of a machine-learning (ML) architecture 2100 used by the data analytics method 2000. In practice, the motion data and the related data analytics are used to detect patterns and determine a probability of injury, based on workload on the feet, number of sessions, etc. The ML architecture 2100 is a merely an example. The ML architecture 2100 includes a central ML pipeline 2102, a data preprocessor 2104, a data processor 2106, and a classifier 2108. Motion data is fed into the ML architecture 2100 to generate features and analytics of the data.

In some embodiments, initially, unsupervised ML techniques may be used to detect data groups between individuals, without any additional inputs other than raw motion data from the insole layer 120. Due to the nature of unsupervised learning, there is no information regarding the ML decision-making process. The unsupervised groupings will separate athletes with similar movement characteristics that is usd to deepen insight from concurrently collected injury data. The user or the user's practitioner can collaborate with the team to standardize the recording process for athletes presenting with musculoskeletal (MSK) complaints or injury, throughout the season. MSK complaint and injury data may then be used as inputs for a supervised ML model aimed at detecting the probability of an athlete having MSK complaint or injury in subsequent training sessions.

The motion data generated may also be synchronized with data generated by another wearable device using time stamps to train a decision-tree classifier or a neural network model that predicts the user's performance and likelihood of injury. The decision-tree classifier is a supervised machine-learning technique that involves asking a series of questions based on different variables to reach a conclusion. The variables include a user's previous health issues, the total distance they have covered in a session and the distance covered at high speed, for an athletic session as an example. Other variations that can be used for decision-tree-based methods, are 'random forest' or 'gradient boosting' techniques, which use multiple decision trees to incrementally improve forecasts. Another machine-learning technology, known as deep neural networks, could yield even greater accuracy.

Advantageously, the systems and methods of monitoring human foot performance enables continuously measuring and understanding dynamic stress load, particularly cumulative lower limb loading and balance. Further, the systems and methods differentiate between changes in external loading experienced by the user, as well as limb-to-limb symmetry in loading. This aids in generating contexts and insights for a user, particularly in metrics related to load, force distribution, and gait. This helps the users, medical practitioners, and coaches gain a deeper understanding of the physical demands during training, open play, rehabilitation sessions, as well as prevent and predict injuries.

Although the disclosed embodiments have been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

While various embodiments of the present disclosure have been described above, it should be understood that they have been presented by way of example only, and not limitation. Numerous changes to the disclosed embodiments can be made in accordance with the disclosure herein, without departing from the spirit or scope of the disclosure. Thus, the breadth and scope of the present disclosure should not be limited by any of the above described embodiments. Rather, the scope of the disclosure should be defined in accordance with the following claims and their equivalents.

What is claimed is:

1. An insole layer comprising:
   a top cover layer;
   a bottom cover layer; and
   a flexible printed circuit board disposed between the top cover layer and the bottom cover layer, wherein the flexible printed circuit board has a single layer with a top surface in direct contact with the top cover layer and the single layer has a bottom surface in direct contact with the bottom cover layer, and
   wherein the flexible printed circuit board includes a rear portion having concave edges and a plurality of kerf bend cuts for (i) forming a concave pattern around the concave edges of the rear portion of the flexible printed circuit board, wherein the plurality of kerf bend cuts forming the concave pattern are parallel to the concave edges of the rear portion, (ii) separating a central enclosure from the rear portion, and (iii) enabling longitudinal bending of a front portion of the flexible printed circuit board, and wherein
   the flexible printed circuit board comprising:
      a motion-tracking device having a plurality of sensors, wherein each sensor is configured to detect motion of one of a plurality of sensing areas disposed adjacent to a lower surface of the flexible printed circuit board;
      a processor configured to receive motion data generated by the motion-tracking device; and
      a power supply device coupled to the motion-tracking device and the processor.

2. The insole layer of claim 1, wherein the insole layer is shaped to be placed inside a shoe, a sock, or under an existing insole of a shoe and is removable to be placed inside another shoe, sock or existing insole.

3. The insole layer of claim 1, wherein the insole layer has a shape customized to correspond to a foot of a user.

4. The insole layer of claim 1, wherein the top cover layer and the bottom cover layer are formed from a water-resistant polyester material.

5. The insole layer of claim 1, wherein each of the top cover layer and the bottom cover layer includes a slippery upper surface and a slip-resistant lower surface.

6. The insole layer of claim 5, wherein the slip-resistant lower surface is formed by a rubber layer disposed under each of the top cover layer and the bottom cover layer.

7. The insole layer of claim 1, wherein the flexible printed circuit board is formed from a glass-reinforced epoxy laminate material.

8. The insole layer of claim 1, further comprising a layer of ethylene propylene diene monomer (EPDM) foam disposed between the flexible printed circuit board and the bottom cover layer.

9. The insole layer of claim 1, wherein the plurality of sensors include:
(i) one or more force-sensitive resistors, (ii) one or more three-axis accelerometers, (iii) one or more three-axis gyroscopes, (iv) one or more magnetometers, (v) one or more temperature sensors, (vi) one or more electromyography sensors, (vii) one or more heart rate sensors, or (viii) any combination thereof.

10. The insole layer of claim 9, wherein the one or more three-axis accelerometers includes at least one high-G accelerometer.

11. The insole layer of claim 1, wherein a distribution of the plurality of sensing areas on the lower surface of the flexible printed circuit board corresponds to pressure points on the foot of the user.

12. The insole layer of claim 1, wherein flexible printed circuit board further comprises a central enclosure for housing (i) the motion-tracking device, (ii) the power supply device, (iii) the processor, or (iv) any combination thereof.

13. The insole layer of claim 12, wherein the central enclosure comprises an upper frame, a lower frame, and a covering plate coupled to the lower frame.

14. The insole layer of claim 1, wherein the flexible printed circuit board further comprises (i) a front sensor module adjacent to a front portion thereof and (ii) a rear sensor module adjacent to a rear portion thereof and electronically connected to the front sensor module, wherein each of the front sensor module and the rear sensor module includes one or more of the plurality of sensing areas and one or more ventilation openings.

15. The insole layer of claim 14, wherein each of the one or more ventilation openings are covered by a waterproof membrane.

16. The insole layer of claim 14, wherein each of the plurality of sensing areas includes a load concentrator encapsulated within an adhesive film.

17. The insole layer of claim 1, wherein the power supply device is a rechargeable lithium polymer battery.

18. The insole layer of claim 1, wherein the flexible printed circuit board further comprises a charging socket configured to charge the power supply device by direct current (DC) charging.

19. The insole layer of claim 18, wherein the charging socket is disposed adjacent to a rear portion of the flexible printed circuit board.

20. The insole layer of claim 18, wherein the charging socket comprises an attachment bracket having:
one or more cutouts for placing magnetic attachments of a DC charging station; and
one or more through-holes to accommodate guide pins of the DC charging station.

21. The insole layer of claim 20, wherein the DC charging station is (i) a stationary rack module, or (ii) a portable sleeve module.

22. The insole layer of claim 1, further comprising a radio-frequency (RF) transmitting antenna and a RF receiving antenna for bidirectional RF communication that enables (i) data exchange with an external computing device, (ii) wireless charging of the power supply device, or (iii) both.

23. The insole layer of claim 1, wherein the flexible printed circuit board further includes a router device for enabling wireless internet communication.

24. The insole layer of claim 1, wherein the flexible printed circuit board further comprises a piezoelectric energy-harvesting device including a piezoelectric force plate configured to convert the kinetic energy generated through movement of the insole layer into electrical energy for charging the power supply device.

25. The insole layer of claim 1, further comprising:
a non-transitory processor-readable memory coupled to the processor, the non-transitory processor-readable memory comprising machine-readable instructions stored thereon that, when executed by the processor, causes the processor to:
encrypt the generated data from the motion-tracking device; and
upload the encrypted data to a block chain, or an external computing device over a wireless communication channel.

26. The insole layer of claim 25, wherein the machine-readable instructions when executed by the processor, further causes the processor to:
download data from an external computing device over the wireless communication channel; and
decrypt the downloaded data.

27. The insole layer of claim 1, wherein the data generated by the motion-tracking device is used by (i) the processor, (ii) a user computing device, (ii) an external computing device, or (iv) any combination thereof, to present interactive visualizations on the motion of the user.

28. The insole layer of claim 1, wherein the data generated by the motion-tracking device is used by (i) the processor, (ii) a user computing device, (iii) an external computing device, or (iii) any combination thereof, to provide a predictive feedback on the motion of the feet of the user, the predictive feedback determined by a machine learning algorithm.

29. The insole layer of claim 28, wherein the machine learning algorithm is one of: (i) a supervised algorithm, or (ii) an unsupervised algorithm.

30. The insole layer of claim 1, wherein the plurality of sensors include a first sensor in a first area and a second sensor in a second area, wherein the first sensor includes a first load concentrator having a first thickness, and the second sensor incudes a second load concentrator having a second thickness different from the first thickness.

* * * * *